(12) United States Patent
Barnes et al.

(10) Patent No.: US 11,288,795 B2
(45) Date of Patent: Mar. 29, 2022

(54) ASSESSING RISK OF BREAST CANCER RECURRENCE

(71) Applicants: Ventana Medical Systems, Inc., Tucson, AZ (US); The Board of Trustees of the Leland Stanford Junior University, Palo Alto, CA (US)

(72) Inventors: Michael Barnes, San Francisco, CA (US); Srinivas Chukka, San Jose, CA (US); David Knowles, Menlo Park, CA (US)

(73) Assignee: Ventana Medical Systems, Inc., Tucson, AZ (US)

(*) Notice: Subject to any disclaimer, the term of this patent is extended or adjusted under 35 U.S.C. 154(b) by 338 days.

(21) Appl. No.: 16/659,545

(22) Filed: Oct. 21, 2019

(65) Prior Publication Data
US 2020/0126222 A1 Apr. 23, 2020

Related U.S. Application Data

(60) Division of application No. 15/374,998, filed on Dec. 9, 2016, now Pat. No. 10,489,904, which is a
(Continued)

(51) Int. Cl.
*G06T 7/00* (2017.01)
*G06K 9/00* (2006.01)
(Continued)

(52) U.S. Cl.
CPC .......... *G06T 7/0012* (2013.01); *C12Q 1/6886* (2013.01); *G06K 9/00147* (2013.01);
(Continued)

(58) Field of Classification Search
None
See application file for complete search history.

(56) References Cited

U.S. PATENT DOCUMENTS

| | | |
|---|---|---|
| 6,358,682 B1 | 3/2002 | Jaffee et al. |
| 7,190,818 B2 | 3/2007 | Ellis et al. |
| | (Continued) | |

FOREIGN PATENT DOCUMENTS

| | | |
|---|---|---|
| WO | 2014140070 A2 | 9/2014 |
| WO | 2014140085 A1 | 9/2014 |

OTHER PUBLICATIONS

Linke, Steven P., et al. "A multimarker model to predict outcome in tamoxifen-treated breast cancer patients." Clinical cancer research 12.4 (2006): 1175-1183. (Year: 2006).*
(Continued)

*Primary Examiner* — Samah A Beg
(74) *Attorney, Agent, or Firm* — Kilpatrick Townsend & Stockton LLP

(57) ABSTRACT

The subject disclosure presents systems and computer-implemented methods for assessing a risk of cancer recurrence in a patient based on a holistic integration of large amounts of prognostic information for said patient into a single comparative prognostic dataset. A risk classification system may be trained using the large amounts of information from a cohort of training slides from several patients, along with survival data for said patients. For example, a machine-learning-based binary classifier in the risk classification system may be trained using a set of granular image features computed from a plurality of slides corresponding to several cancer patients whose survival information is known and input into the system. The trained classifier may be used to classify image features from one or more test patients into a low-risk or high-risk group.

20 Claims, 12 Drawing Sheets

Related U.S. Application Data continuation of application No. PCT/EP2015/062930, filed on Jun. 10, 2015.

(60) Provisional application No. 62/010,290, filed on Jun. 10, 2014.

(51) Int. Cl.
  *G06K 9/62* (2006.01)
  *C12Q 1/6886* (2018.01)

(52) U.S. Cl.
  CPC .......... *G06K 9/629* (2013.01); *G06K 9/6228* (2013.01); *G06T 2207/10024* (2013.01); *G06T 2207/10056* (2013.01); *G06T 2207/10064* (2013.01); *G06T 2207/20081* (2013.01); *G06T 2207/30024* (2013.01); *G06T 2207/30068* (2013.01); *G06T 2207/30072* (2013.01); *G06T 2207/30096* (2013.01)

(56) References Cited

U.S. PATENT DOCUMENTS

| | | |
|---|---|---|
| 7,943,306 B2 | 5/2011 | Chang et al. |
| 9,873,915 B2 | 1/2018 | Mirza et al. |
| 2004/0259144 A1 | 12/2004 | Prabhu |
| 2005/0100933 A1 | 5/2005 | Erlander et al. |
| 2005/0159896 A1 | 7/2005 | Ishikawa et al. |
| 2005/0287541 A1 | 12/2005 | Nakagawara et al. |
| 2006/0078926 A1 | 4/2006 | Marcelpoil et al. |
| 2006/0141493 A1 | 6/2006 | West et al. |
| 2010/0254589 A1 | 10/2010 | Gallagher |
| 2013/0230230 A1 | 9/2013 | Ajemba et al. |
| 2015/0065362 A1 | 3/2015 | Gyorffy et al. |
| 2015/0102216 A1* | 4/2015 | Roder .................. H01J 49/26 250/282 |
| 2015/0213598 A1 | 7/2015 | Madabhushi et al. |
| 2015/0347702 A1 | 12/2015 | Chukka et al. |
| 2016/0102359 A1 | 4/2016 | Shin et al. |
| 2016/0259883 A1 | 9/2016 | Grinchuk et al. |
| 2016/0260211 A1 | 9/2016 | Gillies et al. |
| 2016/0298197 A1 | 10/2016 | Punyaddera et al. |
| 2016/0312289 A1 | 10/2016 | Anastassiou |
| 2016/0335478 A1 | 11/2016 | Bredno et al. |
| 2017/0178361 A1 | 6/2017 | Berezhna et al. |
| 2017/0270666 A1 | 9/2017 | Barnes et al. |
| 2017/0283873 A1 | 10/2017 | Rico et al. |
| 2017/0343548 A1 | 11/2017 | Bakre et al. |
| 2017/0350895 A1 | 12/2017 | Bremer et al. |
| 2018/0000462 A1 | 1/2018 | Venkatarmani et al. |

OTHER PUBLICATIONS

Basavanhally, Ajay, et al. "Multi-field-of-view strategy for image-based outcome prediction of multi-parametric estrogen receptor-positive breast cancer histopathology: Comparison to Oncotype DX." Journal of pathology informatics 2 (2011). (Year: 2011).*

U.S. Appl. No. 15/374,998 , "Notice of Allowance", dated Jul. 15, 2019, 11 pages.

U.S. Appl. No. 15/374,998 , "Non-Final Office Action", dated Jan. 24, 2019, 18 pages.

Basavanhally, A. et al., Multi-field-of-view strategy for image-based outcome predictionof mutli-parametric estrogen receptor-positive breast cancer histopathology: Camparison to Oncotype DX, Journal of Pathology Informatics, 2011, 1-2, 2.

Beck, Andrew H. et al., "Systematic analysis of breast cancer morphology uncovers stromal features associated with survival." Science translational medicine 3. 108 (2011): 108ra113.

Cuzick, J. et al., "Prognostic value of a combined estrogen receptor, progesterone receptor, Ki-67, and human epidermal growth factor receptor 2 immunohistochemical score and comparison with the Genomic Health recurrence score in early breast cancer", Journal of Clinical Oncology, 2011, 4273-4278, 29.

Demir, C. et al., Automated Cancer Diagnosis Based on Histopathological Images: A Systematic Survey, Technical Report, 2005, 1-16, TR-05-09.

Ghaznavi, Farzad et al., "Digital imaging in pathology: whole-slide imaging and beyond." Annual Review of Pathology Mechanisms of Disease 8 (2013): 331-359.

Giusiano, Sophie et al., "Immunohistochemical profiling of node negative breast carcinomas allows prediction of metastatic risk." International journal of oncology 36.4 (2010): 889-898.

Gurcan, M.N. et al. Histopathological Image Analysis: A Review, IEEE Reviews in Biomedical Engineering, 2009, 147-171, 2.

International Preliminary Report on Patentability dated Dec. 15, 2016 in corresponding PCT/EP2015/062930 filed on Jun. 10, 2015, pp. 1-14.

International Search Report and Written Opinion dated Sep. 2, 2015 in corresponding PCT/EP2015/062930 filed on Jun. 10, 2015, pp. 1-18.

Linke, Steven P et al., "A multimarker model to predict outcome in tamoxifen-treated breast cancer patients." Clinical cancer research 12.4 (2006): 1175-1183.

Metzger, G.J. et al., Development of Multigene Expression Signature Maps at the Protein Level from Digitized Immunohistochemistry Slides, Plos One, 2012, e33520, 7.

Motoda, Hiroshi et al., "Feature Selection, Extraction and Construction: A Data Mining Perspective." Jan. 1998, XP055511335, DOI: 10.1007/978-1-4615-5725-8, ISBN 978-1-4613-7622-4.

Piramuthu, Selwyn et al., "Iterative feature construction for improving inductive learning algorithms." Expert Systems with Applications 36.2 (2009): 3401-3406.

Veta, M. et al., Breast Cancer Histopathology Image Analysis: A Review, IEEE Transactions on Biomedical Engineering, 2014, 1400-1411, 61.

Wang, Chao et al., Identifying survival associated morphological features of triple negative breast cancer using multiple datasets, Journal of the American Medical Informatics Association, 2013, 680-687, 20.

Yuan Yinyin, et al., Quantitative Image Analysis of Cellular Heterogeneity in Breast Tumors Complements Genomic Profiling, Science Translational Medicine, 2012, 162-171, 4.

* cited by examiner

| | |
|---|---|
| V1 = | PR_meanValRedCh |
| V2 = | PR_propPos |
| V3 = | PR_stdDevValNormalizedRed |
| V4 = | PR_meanValGreenCh |
| V5 = | ER_pos2pos |
| V6 = | ER_percentPos |
| V7 = | ER_meanValNormalizedBlue |
| V8 = | ER_meanValNormalizedRed |
| V9 = | ER_angle_term |
| V10 = | ER_blob_density3 |
| V11 = | ER_MinorAxisLength |
| V12 = | ER_meanValGreenCh |
| V13 = | ER_meanValRedCh |
| V14 = | ER_PC1Ratio |
| V15 = | ER_AxisRatio |
| V16 = | ER_nonGT_ratio |
| V17 = | ER_nonGT_pow |
| V18 = | ERxKi67 |
| V19 = | Ki67_percentPos |
| V20 = | Ki67_pos2pos |
| V21 = | Ki67_neg2pos |
| V22 = | ER_neg2neg |
| V23 = | ER_stroma2neg |
| V24 = | ER_num_neighbors_minus_med |
| V25 = | ER_blob_density6 |
| V26 = | ER_blob_density4 |
| V27 = | ER_blob_density2 |
| V28 = | PR_nonGT_pow |
| V29 = | PR_stroma2stroma |
| V30 = | PR_neg2neg |
| V31 = | PR_stroma2neg |
| V32 = | PR_neg2stroma |
| V33 = | PR_num_neighbors_minus_med |
| V34 = | PR_blob_density2 |
| V35 = | PR_blob_density6 |
| V36 = | PR_nonGT_ratio |
| V37 = | PR_mean_distance_minus_med |
| V38 = | PR_meanValACh |
| V39 = | PR_pos2pos |
| V40 = | PR_pos2neg |
| V41 = | PR_pos2stroma |
| V42 = | ER_Annulus2 |
| V43 = | ER_pos2neg |
| V44 = | ER_pos2stroma |
| V45 = | PR_Annulus2 |
| V46 = | PR_Annulus1 |
| V47 = | PR_nonGT_area |
| V48 = | PR_blob_density8 |
| V49 = | PR_meanValNormalizedRed |
| V50 = | PR_neg2pos |
| V51 = | ER_StainedCount |
| V52 = | ER_Annulus3 |
| V53 = | ER_neg2pos |
| V54 = | ER_propPos |
| V55 = | ER_Annulus1 |
| V56 = | ER_stdDevValNormalizedRed |
| V57 = | PRxKi67 |
| V58 = | ERxPR |
| V59 = | PR_StainedCount |
| V60 = | PR_percentPos |
| V61 = | ER_seed_vote |
| V62 = | ER_mean_distance_minus_med |
| V63 = | PR_AxisRatio |
| V64 = | PR_PC1Ratio |
| V65 = | PR_mean_dist |
| V66 = | PR_blob_density1 |
| V67 = | Ki67_StainedCount |
| V68 = | Ki67_pos2neg |
| V69 = | Ki67_neg2neg |
| V70 = | Ki67_sizePos |
| V71 = | ER_mean_dist |
| V72 = | ER_meanValACh |
| V73 = | PR_sizePos |
| V74 = | PR_seed_vote |
| V75 = | PR_blob_density3 |
| V76 = | PR_MinorAxisLength |
| V77 = | ER_blob_density1 |
| V78 = | ER_sizePos |
| V79 = | ER_neg2stroma |
| V80 = | ER_stroma2stroma |

FIG. 5C  [ CONTINUATION ]

| | |
|---|---|
| H1 = | PR_meanValRedCh |
| H2 = | PR_propPos |
| H3 = | PR_stdDevValNormalizedRed |
| H4 = | PR_meanValGreenCh |
| H5 = | ER_pos2pos |
| H6 = | ER_percentPos |
| H7 = | ER_meanValNormalizedBlue |
| H8 = | ER_meanValNormalizedRed |
| H9 = | ER_angle_term |
| H10 = | ER_blob_density3 |
| H11 = | ER_MinorAxisLength |
| H12 = | ER_meanValGreenCh |
| H13 = | ER_meanValRedCh |
| H14 = | ER_PC1Ratio |
| H15 = | ER_AxisRatio |
| H16 = | ER_nonGT_ratio |
| H17 = | ER_nonGT_pow |
| H18 = | ERxKi67 |
| H19 = | Ki67_percentPos |
| H20 = | Ki67_pos2pos |
| H21 = | Ki67_neg2pos |
| H22 = | ER_neg2neg |
| H23 = | ER_stroma2neg |
| H24 = | ER_num_neighbors_minus_med |
| H25 = | ER_blob_density6 |
| H26 = | ER_blob_density4 |
| H27 = | ER_blob_density2 |
| H28 = | PR_nonGT_pow |
| H29 = | PR_stroma2stroma |
| H30 = | PR_neg2neg |
| H31 = | PR_stroma2neg |
| H32 = | PR_neg2stroma |
| H33 = | PR_num_neighbors_minus_med |
| H34 = | PR_blob_density2 |
| H35 = | PR_blob_density6 |
| H36 = | PR_nonGT_ratio |
| H37 = | PR_mean_distance_minus_med |
| H38 = | PR_meanValACh |
| H39 = | PR_pos2pos |
| H40 = | PR_pos2neg |
| H41 = | PR_pos2stroma |
| H42 = | ER_Annulus2 |
| H43 = | ER_pos2neg |
| H44 = | ER_pos2stroma |
| H45 = | PR_Annulus2 |
| H46 = | PR_Annulus1 |
| H47 = | PR_nonGT_area |
| H48 = | PR_blob_density8 |
| H49 = | PR_meanValNormalizedRed |
| H50 = | PR_neg2pos |
| H51 = | ER_StainedCount |
| H52 = | ER_Annulus3 |
| H53 = | ER_neg2pos |
| H54 = | ER_propPos |
| H55 = | ER_Annulus1 |
| H56 = | ER_stdDevValNormalizedRed |
| H57 = | PRxKi67 |
| H58 = | ERxPR |
| H59 = | PR_StainedCount |
| H60 = | PR_percentPos |
| H61 = | ER_seed_vote |
| H62 = | ER_mean_distance_minus_med |
| H63 = | PR_AxisRatio |
| H64 = | PR_PC1Ratio |
| H65 = | PR_mean_dist |
| H66 = | PR_blob_density1 |
| H67 = | Ki67_StainedCount |
| H68 = | Ki67_pos2neg |
| H69 = | Ki67_neg2neg |
| H70 = | Ki67_sizePos |
| H71 = | ER_mean_dist |
| H72 = | ER_meanValACh |
| H73 = | PR_sizePos |
| H74 = | PR_seed_vote |
| H75 = | PR_blob_density3 |
| H76 = | PR_MinorAxisLength |
| H77 = | ER_blob_density1 |
| H78 = | ER_sizePos |
| H79 = | ER_neg2stroma |
| H80= | ER_stroma2stroma |

FIG. 5C  [ CONTINUATION ]

ASSESSING RISK OF BREAST CANCER RECURRENCE

PRIORITY TO RELATED APPLICATIONS

This patent application is a divisional of U.S. patent application Ser. No. 15/374,998 filed Dec. 9, 2016 which is a continuation of International Application No. PCT/EP2015/062930 filed Jun. 10, 2015, which claims priority to and the benefit of U.S. Provisional Application No. 62/010,290, filed Jun. 10, 2014. Each of the above patent applications is incorporated herein by reference as if set forth in its entirety.

BACKGROUND OF THE SUBJECT DISCLOSURE

Field of the Subject Disclosure

The present subject disclosure relates to a computer-implemented method and/or digital pathology enabled machine learning system for predicting the risk of cancer recurrence in early stage breast cancer patients. More particularly, the present subject disclosure relates to predicting breast cancer recurrence risk directly from a set of image features computed from digitized immunohistopathology (for example, H&E, IHC) tissue slides.

Background of the Subject Disclosure

Prognosis of hormone-positive early-stage breast cancer patients offers the opportunity to make more informed follow-up choices, for example the addition of adjuvant chemotherapy. Traditionally, pathologists have prognosticated these cancers using conventional staging, tumor proliferation index, and a small set of morphological features (gland formation, nuclear grade, and mitosis) that are manually scored from H&E slides. Alternatively, in some prior art methods, image-features computed directly from the H&E slide only are utilized to train a machine learning module to build a prognostic model to predict overall survival in breast cancer patients. For further breast cancer subtyping and prognostic and predictive evaluation, protein expression of the tumor is evaluated by analyzing the patient immunohistochemical (IHC) tissue slides. Hormone-positive status of the cancer is determined from interpreting the estrogen receptor (ER) and progesterone receptor (PR) marker slides. Tumor proliferation and aggressive nature of the tumor is determined from Ki67 biomarker tissue slide. The patient's suitability to targeted therapy (such as Herceptin) is determined by analyzing the HER2 IHC tissue slide. The information inferred from the H&E tissue slide, along with the immunohistochemical (IHC) protein expression of the tumor, such as estrogen receptors (ER), progesterone receptors (PR), HER2, and Ki67 markers, given as IHC marker slide-level quantitative scores such as either (marker) percent positivity or H-score, may be used to prognosticate a patient.

The classification of breast cancer based on Estrogen receptor (ER) and HER2 testing is as such known from the prior art, cf. http://www.cancer.org/cancer/breastcancer/detailedguide/breast-cancer-classifying.

Prior art methods for tissue slide based diagnostics such as those disclosed in Jack Cuzick, et al, Prognostic Value of a Combined Estrogen Receptor, Progesterone Receptor, Ki-67, and Human Epidermal Growth Factor Receptor 2 Immunohistochemical Score and Comparison With the Genomic Health Recurrence Score in Early Breast Cancer, JCO Nov. 10, 2011:4273-4278; published online on Oct. 11, 2011 at http://jco.ascopubs.org/content/29/32/4273.long. The cited reference discloses predicting breast cancer risk of recurrence using slide-level clinical scores computed from IHC slides (ER, PR, Ki67 and HER2). Individual IHC marker slides are scored (either manually or algorithmically) and slide level scores of percent positivity and H-score are computed. Using the slide level scores (percent positivity, H-scores) from the four markers, an IHC4 metric is computed. Based on the computed value of the IHC4 score/metric, the patient is categorized as belonging to low/high recurrence risk group.

While there is potentially a large amount of prognostic information for a given patient tissue sample, typically each sample-containing slide is analyzed separately from a clinical standpoint and summarized in few quantitative metrics such as percent positivity and H-score, without systematic evaluation and holistic integration of all the information contained in the tissue into a single comparative prognostic.

SUMMARY OF THE SUBJECT DISCLOSURE

The present disclosure provides an image processing method that uses a trained predictor for signaling a requirement for adjuvant chemotherapy and a respective method for training the predictor. Furthermore, the disclosure relates to image processing systems. Additional aspects of the disclosure are set forth in the further independent claims. These aspects may be combined with the preceding independent and/or dependent claims.

Embodiments of the disclosure are particularly advantageous as prognostic features are determined that are useful for classifying a patient into a high or a low risk group using a data-driven approach. This is accomplished by computing a large number of inter-marker features, such as several hundred inter-marker features, by calculating combinations of acquired marker-specific biological features.

These combinations can be obtained by a 'brute-force' approach, i.e. by using a large number of all possible arbitrary combinations that can be formed from the marker-specific biological features or an arbitrary random selection of marker-specific biological features to calculate the combinations. Heuristics may or may not be used to select the combinations. The calculation of the combinations can be performed by one or more mathematical operations which can be elementary or complex, such as by multiplying the values of two marker-specific biological features or by calculating a correlation coefficient being descriptive of a correlation, such as a spatial correlation, of the marker-specific biological features of such a pair.

In particular, different combinations using different mathematical operations can be calculated for the same pair resulting in a large data value of inter-marker features. Such a large database is obtained even if the number of the available tissue samples for performing the training of the predictor is limited.

In accordance with an embodiment of the disclosure, the sub-set of the marker-specific biological features and the inter-marker features that are entered into the predictor for its training is selected and output by the predictor such as by L1-regularized logistic regression. This way a sub-set of the marker-specific biological features and the inter-marker features is identified to be prognostic features that are useful for classifying the patient into a high or low risk group.

This data-driven approach is particularly useful as the resultant prognostic features do not need to be based on a biological understanding of the underlying biological processes. Even though biological knowledge as regards the interplay of the identified prognostic features may not be available and the reason why the prognostic features are in fact useful is unknown, embodiments of the present disclosure still provide such a prognostic feature combination due to the data-driven approach.

Surprisingly this enables to predict whether a given patient belongs to a low risk group such that hormone therapy alone is sufficient and chemotherapy and its adverse side-effects can be avoided.

It is to be noted that in the prior art an adjuvant chemotherapy is always administered to breast cancer patients in addition to hormone therapy as about 15% of breast cancer patients are not responsive to hormone therapy. As there is no way in the prior art to reliably predict whether a patient belongs to a low or high risk group, chemotherapy is always given as an adjuvant therapy. Thus, the present disclosure greatly reduces unnecessary hardship experienced by cancer patients as embodiments of the disclosure enable to identify those patients that actually do require chemotherapy such that administration of chemotherapy can be avoided for the majority of patients.

A 'tissue sample' as understood herein is any biological sample, such as a surgical specimen that is obtained from a human body for anatomic pathology.

A 'multi-channel image' as understood herein encompasses a digital image obtained from a biological tissue sample in which different biological structures, such as nuclei and tissue structures, are simultaneously stained with specific fluorescent dyes, each of which fluoresces in a different spectral band thus constituting one of the channels of the multi-channel image. The biological tissue sample may be stained by a plurality of stains and/or by a stain and a counterstain, the latter being also referred to as a "single marker image."

An 'unmixed image' as understood herein encompasses a grey-value or scalar image obtained for one channel of a multi-channel image. By unmixing a multi-channel image one unmixed image per channel is obtained.

'Early stage breast cancer' as understood herein encompasses breast cancer that has not spread beyond the breast or the axillary lymph nodes. This includes ductal carcinoma in situ and stage I, stage IIA, stage IIB, and stage IIIA breast cancers.

'Survival data" as understood herein encompasses breast cancer recurrence data, i.e. the recurrence of breast cancer at a location that is different from the one from which the tissue sample has been obtained, such as recurrence that is due to metastasized cancer.

A 'pair of marker-specific biological features" encompasses a set of two or more marker-specific biological features, such as an n-tuple of marker-specific biological features.

Disclosed herein are computer-implemented methods and machine learning systems for assessing a risk of cancer recurrence in a patient based on a holistic integration of large amounts of information for said patient into a single comparative prognostic. The large amounts of information may be analyzed from H&E and commonly used immunohistochemistry (IHC) tissue slides, as well as other IHC slides such as immune panel slides, etc. A machine learning system for risk classification may be trained using the large amounts of information from a cohort of training slides from several patients, along with clinical and survival data for said patients. For example, a machine-learning-based binary classifier in the risk classification system may be trained using a large and varied set of intra and inter-marker image features computed from a plurality of whole slides corresponding to several cancer patients whose clinical diagnostic attributes and survival information is known and input into the system. The set of image features computed from digitized images of an H&E slide and one or more IHC tissue slides from a biological specimen, such as breast tissue, that has been placed on a substrate, such as a slide. The trained classifier may be used to classify image features from one or more test patients into a low-risk or high-risk group. Therefore, the disclosed risk classification system may be invoked to categorize a biological specimen from a test patient as belonging to a low risk or high risk group for cancer recurrence. Such novel methods disclosed herein may be contrasted with looking solely at IHC slide images and scoring at slide level/tumor grading using known grossly descriptive and slide-level semi-quantitative metrics such as percent positivity, stain intensity, and H-score, and binning the score into a positive or negative, as part of current standard clinical practice, that has not adequately addressed the problem of predicting the recurrence of risk in early stage breast cancer patients using the comprehensive feature generation and systematic discovery and holistic combination of the whole slide tissue features disclosed herein.

In one exemplary embodiment, the subject disclosure comprises a system for determining a risk of breast cancer recurrence, the system comprising a processor and a memory coupled to the processor, the memory to store computer-readable instructions that, when executed by the processor, cause the processor to perform operations comprising computing a plurality of marker-specific features and a plurality of inter-marker features from one or more images corresponding to a tissue sample, wherein at least a first image of said one or more images is an H&E image and at least a second image of said one or more images is one of an individually stained or a multiplex IHC image, wherein the marker-specific features are related to tissue objects in each image, and wherein each of the inter-marker features are relative to the tissue objects present in both images, and training a breast cancer recurrence predictor model with a combination of the plurality of marker-specific features and the plurality of inter-marker features along with survival data for a patient associated with the tissue sample, wherein the trained breast cancer recurrence predictor model may subsequently be applied to a test image received for analysis to determine a breast cancer risk of recurrence score.

In another exemplary embodiment, the subject disclosure includes a method for selecting features for a breast cancer recurrence prediction model, said method comprising utilizing a computer-implemented machine learning tool for performing operations comprising generating a prediction rule based on training data for a cohort of patients whose breast cancer outcomes are at least partially known, wherein for each patient the training data comprises measurements for a set of features, and one or more breast cancer outcomes with respect to said patient, and refining the prediction rule using a combination of a bootstrap analysis and a cross-validation, wherein the prediction rule may subsequently be applied to a test image received for analysis to determine a breast cancer risk of recurrence score.

In yet another exemplary embodiment, the subject disclosure includes a tangible non-transitory computer-readable medium to store computer-readable code that is executed by a processor to perform operations comprising computing a plurality of features from one or more images corresponding to a tissue sample, wherein at least a first image of said one or more images is an H&E morphological image and at least a second image of said one or more images is one of an individually stained or a multiplex IHC image, and training a breast cancer recurrence predictor model with a combination of the plurality of features along with survival data for a patient associated with the tissue sample, wherein the trained breast cancer recurrence predictor model may subsequently be applied to a test image received for analysis to determine a breast cancer risk of recurrence score.

In yet another exemplary embodiment, the subject disclosure includes a tangible non-transitory computer-readable medium to store computer-readable code that is executed by a processor to perform operations comprising computing a plurality of features from one or more images corresponding to a tissue sample, wherein at least a first image of said one or more images is a morphological image and at least a second image of said one or more images is one of an individually stained or a multiplex IHC image, wherein the plurality of features comprises at least one of a nucleus blob shape features, a nucleus blob area feature, a nucleus blob compactness feature, a nucleus blob density feature, a normalized color feature, an absolute color feature, a center vote strength, an annular region based feature, or a blob topography feature, and training a breast cancer recurrence predictor model with a combination of the plurality of features along with survival data for a patient associated with the tissue sample, wherein the trained breast cancer recurrence predictor model may subsequently be applied to a test image received for analysis to determine a breast cancer risk of recurrence score.

DETAILED DESCRIPTION OF THE SUBJECT DISCLOSURE

Systems and methods disclosed herein relate to determining the risk of cancer recurrence. A classifier, such as a machine learning module, may be trained using a holistic integration of large amounts of prognostic feature information for one or more patients into a single comparative prognostic dataset. The large amounts of information may be analyzed from H&E and commonly used immunohistochemistry (IHC) slides, as well as other IHC slides such as immune panel slides, etc. A risk classification system may be trained using the large amounts of information from a cohort of training slides from several patients, along with clinical and survival data for said patients. For example, a machine-learning-based binary classifier in the risk classification system may be trained using a set of image features computed from a plurality of slides corresponding to several cancer patients whose clinical diagnostic and survival information is known and input into the system. The set of image features computed from digitized images of an H&E slide and one or more IHC tissue slides from a biological specimen, such as breast tissue, that has been placed on a substrate, such as a slide. The trained classifier may be used to classify image features from one or more test patients into a low-risk or high-risk group of risk of recurrence. Therefore, the disclosed risk classification system may be invoked to categorize a biological specimen from a test patient as belonging to a low risk or high risk group for cancer recurrence.

Although the disclosed embodiments are described for exemplary purposes in connection with the identification of breast cancer tumors and for use in risk or likelihood of breast cancer recurrence computations using markers such as ER, PR, HR, and Ki67, other tumor markers may be used. Moreover, the subject disclosure is applicable to images of biological specimens that have been stained with fluorescent and non-fluorescent stains, or any type of microscopic image capture (brightfield, fluorescence, darkfield, etc.), and either as a whole slide or partial slide, i.e. with one or more selected regions or fields of view (FOVs) on each slide, as will become evident to persons having ordinary skill in the art upon reading of this disclosure. Further, one of ordinary skill in the art would recognize that the order of the operations disclosed herein may vary from what is described, so long as the inventive scope and spirit of the disclosed embodiments is maintained.

Figure 1:
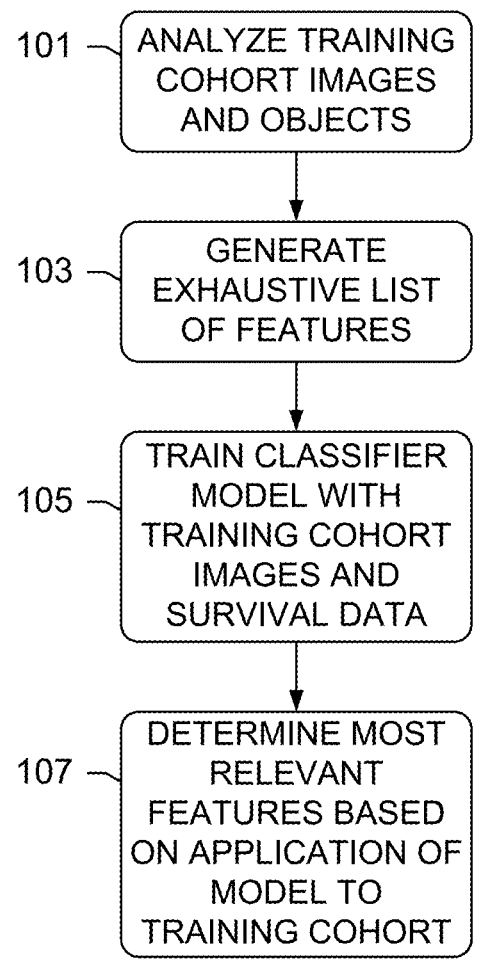
FIG. 1 depicts a method for assessing a risk of cancer recurrence, according to an exemplary embodiment of the subject disclosure.

FIG. 1 depicts a method for assessing a risk of cancer recurrence, according to an exemplary embodiment of the subject disclosure. According to FIG. 1, the method begins with an analysis 101 of training cohort images, and objects depicted thereon. The training cohort images may be from patients that have been diagnosed as being ER+ (hormone positive) and HER2 negative. Generally, the IHC images may include any of H&E, ER, PR, HER2, and Ki67 images from each patient. For instance, in most cases, the images comprise a first image including an H&E image, and the second, third, etc. images comprise one or more IHC images, which can be either from single stained or multi-plexed stained tissue slides. The training cohort consists of several early stage breast cancer patients, for example, between 100 and 200 patients. The training cohort images are intended to be provided into a training operation 105 along with survival data of each patient, such as known clinical outcomes, how long the patient survived, how well they responded to drugs, etc. The survival data may include, for instance, Kaplan-Meyer survival curves for 20 years of cancer recurrence.

For example, for each patient the information may include:

a) Histopathological Tissue Data comprising H&E and IHC tissue whole slides (H&E, ER, PR, Ki67 and HER2)

b) Clinical information comprising age, tumor grade, tumor stage, date when breast cancer is initially diagnosed, treatment dates, if and when hormone therapy is given, if and when chemotherapy given, if the cancer has metastasized (i.e. the cancer has been found in other parts of the body), if and when the cancer has recurred in the time of observation (10 to 20 years of observations), etc. From the given clinical information, for each patient, it can be inferred whether or not the cancer has recurred in the patient, and the recurrence time.

Prior to training, an exhaustive list of features is generated 103 for the several tissue structures depicted in the images. Details about the features are provided herein, and generally include presence, characteristics, and inter-structural relationships of positively/negatively stained nuclei, lymphocytes, stromal cells, etc. The feature generation 103 includes computing low-level/granular features (size, shape, relational features) for the detected structures for each patient, whether within a single marker slide, or between multiple marker slides associated with the same patient (inter-marker features). Several thousand image features may be computed on the detected tissue objects using image analysis algorithms as further described herein.

The images, features, and survival data are input into a machine learning module to generate a classifier model 105. This process, also further described herein, includes correlating the feature matrix, i.e. the exhaustive set features from all the patients, with breast cancer recurrence data, also considered as training ground truths for the classifier. For example, by defining a 5-yr recurrence time point as the cutoff, the patient population is categorized into two groups—low-risk and high risk (of recurrence) groups, and the two groups of low-risk and high-risk patients are input into a machine learning algorithm to train a binary classifier to classify the patient population into two groups of low-risk and high-risk (of recurrence) patients based on the image features computed from the slides. In other words, the feature data and clinical outcome/survival data are input into the machine learning module, resulting in a trained classifier that may be used to predict new slide prognosis of a test patient based on a combination of the features 107. Moreover, correlating the feature list against the known survival data of the training cohort enables a determination of which granular features count the most towards the survival outcomes to enable discrimination between the low and risk categories. Such "feature selection" and automatic determination of the weights of the parameters to combine the discriminant prognostic features to give the optimal separation of the combined value between that of low and risk categories is enabled by machine learning statistical methods such as L1 regularized logistic regression, i.e. the "lasso" as further described herein, and further verifying and validating the output prognostic model by cross validating and evaluating the performance by computing receiver-operating-characteristic (ROC) curve to bolster the model by ensuring that the model is not overfitting to any particular training cohort, and provides consistent results for any independent and unseen dataset. Cross-validation, for example, trains the model from a subset of cases from the training cohort, and tests on another subset or remaining subset. The process may be repeated several times to ensure there is no overfitting and the model produces similar results on any independent test set. For example, the ROC curve indicates how robust the algorithm performance is by clearly quantifying the performance of positive outcomes and negative outcomes, so as to discourage false positives and true negatives.

Hence, the machine learning statistical method such as L1 regularized logistic regression, provides prognostic marker-specific biological features and prognostic inter-marker specific features as a sub-set of the original marker-specific biological features and large number of inter-marker specific features whereby the number of prognostic inter-marker specific features may be drastically below the original number of inter-marker specific features.

Figure 2:
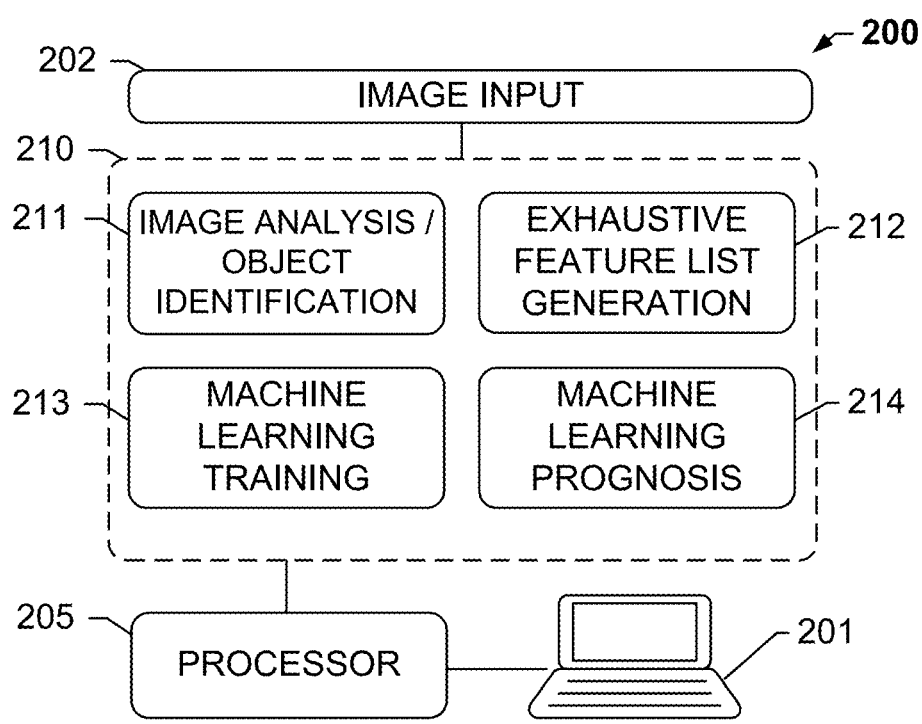
FIG. 2 depicts a system 200 for assessing a risk of cancer recurrence, according to an exemplary embodiment of the subject disclosure.

FIG. 2 depicts a system 200 for scoring IHC slides and computing a prognostic model, according to an exemplary embodiment of the subject disclosure. System 200 comprises a memory 210, which stores a plurality of processing modules or logical instructions that are executed by processor 205 coupled to computer 201. Execution of one or more of the plurality of processing modules 211-214 may be triggered by receiving image data from image input 202 or any other input such as a user input. Besides processor 205 and memory 210, computer 201 also includes user input and output devices such as a keyboard, mouse, stylus, and a display/touchscreen. As will be explained in the following discussion, processor 205 executes logical instructions stored on memory 210.

Image input 202 may include any means for receiving an image of a tissue specimen mounted on a slide. One such means may include any combination of a staining and/or imaging platform. For instance, the specimen may have been stained by means of application of a staining assay containing one or more different biomarkers associated with chromogenic stains for brightfield imaging or fluorophores for fluorescence imaging. Staining assays can use chromogenic stains for brightfield imaging, organic fluorophores, quantum dots, or organic fluorophores together with quantum dots for fluorescence imaging, or any other combination of stains, biomarkers, and viewing or imaging devices. A typical specimen is processed in an automated staining/assay platform that applies a staining assay to the sample, resulting in a stained sample. There are a variety of commercial products on the market suitable for use as the staining/assay platform, one example being the Discovery® product of the assignee Ventana Medical Systems, Inc. Image input 202 may further include a camera on a microscope or a whole-slide scanner having a microscope and/or imaging components, such as the Ventana iScan HT or iScan Coreo scanners enabled to whole slide scan tissue slides at 20× or 40× magnifications.

Alternatively or in addition, image input 202 may include a network or any other communications means for providing digitized images of whole-slides to memory 210 for processing by the modules stored thereon.

In either case, the images may further include a training cohort that consists of a set of immuno-histopathology tissue slides from multiple early breast cancer patients along with their clinical outcome data. The clinical outcome data is the observed patient survival data over a time span of several years. For each training patient, H&E and a set of IHC tissue slides (ER, PR, Ki67, HER2 and any of the immune panel slides) are input. The training cohort is used to train a classifier using machine learning training module 213 stored on memory 210.

An image analysis/object identification module 211 may be invoked to analyze the individual marker slides to detect and classify the various tissue objects, such as cells, glands and tissue regions. The image analysis may be performed on a whole-slide image, or on designated fields of view (FOVs) within the images. For example, rather than digitizing the whole slide using a whole slide scanner at the desired magnification of 20/40×, a pathologist can review the slide under a digital microscope and select regions for image analysis and capture only those regions. Any subsequent image analysis operations described herein may be performed on specified regions or FOVs of the input image. This operation may be provided via an interface for loading an image from memory 210 or any storage device, and selecting fields of view, using a slide management application such as Virtuoso®, ImageViewer®, Verso®, etc. Based upon a careful navigation and review of the whole slide at different magnifications, the pathologist or a qualified expert annotates enough number of representative tumor regions (fields of views, FOVs) on the digitized whole slide for analysis. The annotated representative fields may be selected to reflect the marker expression that the pathologist would use for overall slide interpretation. Annotations may be drawn using an annotation tool provided in the viewer application. The annotations can be drawn at any particular magnification (resolution). Alternatively or in addition, image analysis operations may be used to automatically detect tumor regions or other regions using automated image-analysis operations such as segmenting, thresholding, edge-detection, etc., and FOVs automatically generated based on the detected regions.

Moreover, FOVs may be registered or transferred from one image, such as an H&E image, to a second image of the same patient, such as an IHC image, that depicts an adjacent tissue specimen that is differently stained. Registration operations across assays with different combinations of stains and markers may use an inter-marker algorithm, such as methods further described with reference to commonly-assigned and co-pending EP patent application WO2014140070A2, the contents of which are hereby incorporated herein by reference in their entirety. Relevant sections of the incorporated patent application describe a computerized image registration process comprising selecting a first digital image of a first tissue section from a set of digital images of adjacent tissue sections of a single patient, selecting a second digital image of a second tissue section from the set, matching tissue structure between the first digital image and the second digital image, and automatically mapping an annotation drawn on the first digital image to the second digital image. The first digital image may be derived from an image obtained using a stain and an imaging mode, and the second digital image may be derived from an image obtained using a different stain, a different imaging mode, or both as compared to the first digital image. The stain may be chosen from a hematoxylin and eosin stain ('H&E' stain), an immunohistochemistry stain ('IHC" stain), or a fluorescent stain. The imaging mode may be chosen from brightfield microscopy or fluorescent microscopy. A matching tissue structure may comprise a coarse registration mode comprising: generating a first gray-level tissue foreground image from the first digital image and generating a second gray-level tissue foreground image from the second digital image, computing a first tissue binary edge map from the first gray-level tissue foreground image and computing a second tissue binary edge map from the second gray-level tissue foreground image, computing global transformation parameters to align the first binary edge map and the second binary edge map, and, mapping the first digital image and the second digital image to a common big grid encompassing both the first and second digital images based on the global transformation parameters. Computing global transformation parameters may further comprise using a moments-based mapping method to generate an affine mapping between the first binary edge map and the second binary edge map. A fine registration mode may be used to refine alignment of the first digital image and the second digital image. The fine registration mode comprises: annotating the first digital image, mapping the annotation on the common big grid to a corresponding location in the second digital image, and updating the location using Chamfer-distance matching based on the binary tissue edge maps. Cropped versions of the tissue edge binary maps may be used and the method may further comprise selecting a minimum cost window which improves matching relative to coarse mode registration.

Upon designating a field of view and/or registering the field of view across images, an object-level analysis operation of image analysis module 211 may be invoked to analyze the individual marker slides to detect and classify the various tissue objects, such as cells, glands and tissue regions. This includes counting the number of tumor cells, for instance in a hematoxylin channel that is unmixed or deconvolved from the RGB whole-slide image. Nuclei detection may use any known nuclei detection method, such as segmenting, thresholding, etc. In one exemplary embodiment, a radial symmetry based nuclei detection operation is used. Radial symmetry operations are further described in commonly-assigned and co-pending patent application WO2014140085A1. These operations may include automatically interpreting and scoring tissue specimen slides, for example, specimens stained with an immunohistochemical (IHC) assay. A region of an image or an entire image (e.g., a digital whole-slide image) may be analyzed based at least in part on information and characteristics associated with the whole slide and features selected for quantitative analysis. A whole slide image is considered an image of all or substantially all of the tissue containing regions (e.g., all regions of the slide excluding labels, markers, and blank areas) of a slide. Cellular structures (e.g., nuclear objects, nuclei seed) and cells in a region of a slide (e.g., a particular tissue region of the slide) or the whole slide may be identified based at least in part on information pertaining to data associated with tissue containing regions of the slide. Cells may be counted and various types of local and global features of these cells computed to identify the cell types and perform quantitative analysis. The feature computation can use information from not only an annotated region or FOV of a slide but also information from the whole slide (e.g., tissue-containing regions of the slide analyzed at multiple magnifications). Cells may be automatically counted and classified to score the image and/or entire slide based at least in part on selected fields of view and/or the whole slide based at least in part on information or data associated with the whole slide (i.e., all of the tissue containing regions of the slide).

The object-level analysis may be marker-slide specific and hence provides marker-specific biological features. For example, to analyze ER breast tissue slide, an algorithm specifically designed to analyze images of ER slides is used. The algorithm detects and classifies the "tissue objects" in a particular slide that are specific to the associated marker. Here "tissue objects" generically refer to any meaningful tissue structure of interest such as nucleus, membrane, gland or a specific region such as epithelial or stromal tissue. For example, in an image of an ER tissue slide, the object-level analysis operation may detect nuclei and classify them as the ER-positive stained tumor nuclei, ER-negative stained tumor nuclei, lymphocytes and stromal cells. In one exemplary embodiment, an FDA 510(k) cleared algorithm of the assignee VENTANA® is used to analyze breast tissue ER slide. The VENTANA Companion Algorithm Estrogen Receptor (ER) image analysis algorithm is intended for use as an aid to the pathologist in the detection and semi-quantitative measurement of ER protein in formalin-fixed, paraffin-embedded neoplastic tissue. When used with the CONFIRM anti-ER (SP1) Rabbit Monoclonal Primary Antibody, the ER (SP1) algorithm is indicated for use as an aid in the assessment of breast cancer patients for whom endocrine treatment is being considered, but is not the sole basis for treatment. Any equivalent method to detect and classify nuclei in ER slides may be used instead. Similarly, HER2 image analysis algorithm (e.g., VENTANA HER2 algorithm) detects the HER2 positive membrane stained cells in the HER2 images. For example, an FDA 510(k) cleared VENTANA algorithm may be used to analyze breast panel ER, PR, Ki67 and HER2 slides. Similarly, an H&E image analysis algorithm can be used to a) detect or output H&E Image segmented into different labelled tissue regions such as stromal, connected tissue, tumor and necrotic regions etc.; b) detect and classify nuclei as tumor nuclei, stromal cells and lymphocytes; and/or c) detect epithelial glandular structures by performing glandular segmentation. Such an algorithm is further described in U.S. Provisional Application No. 61/932,671, filed by the assignee VENTANA MEDICAL SYSTEMS, INC.® on Jan. 28, 2014, titled ADAPTIVE CLASSIFICATION FOR WHOLE SLIDE TISSUE SEGMENTATION and PCT/EP2015/051302(P31978-WO (GF)/ROC.214.21 WO) the entirety of which being incorporated herein by reference. Subsequently, a feature-level analysis operation of image analysis module 211 is executed to compute image features for the various tissue objects detected in each marker slide. This encompasses the acquisition of marker-specific biological features from the at least first and second images individually and to compute inter-marker features that relate biological features of different ones of the images to each other by execution of a mathematical operation that uses the numerical values obtained for a pair of the biological features as input values.

These operations include using the captured image information and the detected tissue objects to acquire object-level features and relational features in each marker slide individually. For example, in each marker slide, a set of local and regional morphometric, image intensity and relational features are computed for each object. The local shape features computed for the detected nuclei in an ER slide, for instance, may include shape features such as area, eccentricity, perimeter, orientation etc., and image intensity features include the average stain intensity for the nucleus, the intensity variation within a nucleus etc. A list of typical features is provided herein in this disclosure and in Table 1. As the features are associated with the corresponding tissue objects, the features are also slide-specific. For example, Ki67 tissue slide image data is used to compute the image features for nuclei detected in a Ki67 slide, and the information from an H&E slide is used to compute image features for the regions, glands and nuclei and lymphocytes detected in the H&E slide.

Further, sets of relational inter-marker features between the detected nuclei, glands and regions are computed. These features may include an average distance between any two tumor nuclei that are detected in two different images, or the distance of nucleus to the nearest epithelial region and the distance of a stromal cell to the nearest tumor region, the nearest distance of a tumor nucleus to a lymphocyte cell, the local density of lymphocytes, the local density of tumor nuclei, etc. These and other features identified by the analysis modules are listed in Table 1.

Subsequently, a slide-level analysis operation may be executed to compute aggregate slide-level features from the object-level features computed by the feature-level analysis operation. For each of the object-level feature type computed for each marker, a histogram of the feature values from all the detected tissue objects in the analyzed image is constructed. For each of these features, simple summarizing metrics including but not limited to: average, median, mode, standard deviation, minimum and maximum values, inter quartile range (difference between 75% and 25% percentile locations), and entropy may be computed. A representative set of these marker specific slide-level features is also listed in the list described in this description and in Table 1. Based on the slide-level features computed for each marker, one or more inter-marker co-expression features may be identified and computed by an inter-marker analysis operation. Representative inter-marker features are also listed in Table 1. Subsequently, a case-level analysis operation is executed to compute aggregate case-level features for a slide or plurality of slides associated with a single patient or a case. Case-level features may be collated from the features computed by the slide-level analysis and inter-marker analysis operations. In an exemplary embodiment of the subject disclosure, case-level analysis operations may include concatenating the slide-level features computed for each of the individual markers and inter-marker co-expression features to construct a case-level feature vector for the patient, as further described with respect to FIG. 3A. An exemplary set of all the features listed in Table 1 may collectively constitute case-level features for a patient.

As described herein, a machine-learning-based binary classifier may be trained using a set of image features computed from a plurality of slides corresponding to several cancer patients whose survival information is known and input into the system. This training is enabled by an exhaustive feature list generation module 212, which uses the case-level features for all the patients in the training set to construct a feature matrix for the training dataset. The feature matrix constitutes the feature information gathered from all the patients' slides. In an exemplary embodiment of the subject disclosure, for each patient in the training set, the clinical outcome data has also been observed. The clinical outcome data, which has been obtained, is the patient survival data over a specified time period. The set of cancer patients who are alive beyond a certain time period (e.g., five years), from the date of initial diagnosis, may be defined as a low risk of recurrence group; and similarly, the set of patients who are deceased before the certain period may be considered as the high risk group. Thus, each patient is categorized to be belonging to the low-risk or high-risk group. The patient category label information is considered as the ground truth for the machine learning training module 213.

Using the feature matrix and the ground truth vector from the training dataset, machine learning training module 213 trains a binary classifier using supervised learning methodology. In this supervised learning framework, the classifier learns a model which is used to classify a new data sample. The classifier is trained with the above-described training set of user provided examples (i.e. training data) for which, along with the feature data information, the classification label information is also known a priori. Once trained, when applied to an input test sample (or sample) by machine learning prognosis module 214, the classifier predicts the test sample's (or sample's) classification label, as further described with respect to FIG. 6.

As described above, the modules include logic that is executed by processor 205. "Logic", as used herein and throughout this disclosure, refers to any information having the form of instruction signals and/or data that may be applied to affect the operation of a processor. Software is one example of such logic. Examples of processors are computer processors (processing units), microprocessors, digital signal processors, controllers and microcontrollers, etc. Logic may be formed from signals stored on a computer-readable medium such as memory 210 that, in an exemplary embodiment, may be a random access memory (RAM), read-only memories (ROM), erasable/electrically erasable programmable read-only memories (EPROMS/EEPROMS), flash memories, etc. Logic may also comprise digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network. Moreover, the modules need not be executed in any specific order. Each module may call another module when needed to be executed.

Figure 3A:
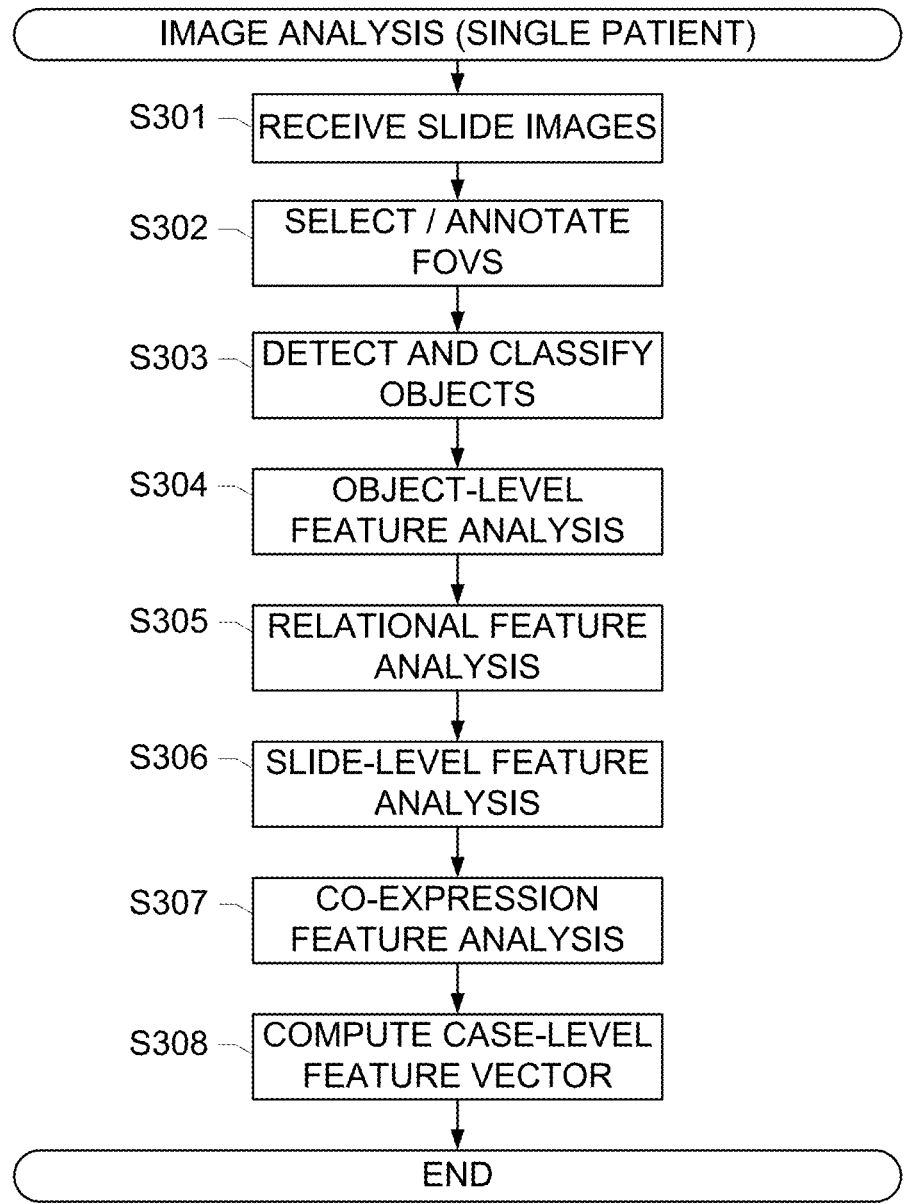
FIGS. 3A-3C respectively depict workflows and methods for detecting tissue objects using image analysis algorithms and determining an exhaustive set of inter and intra-marker image features based on detected tissue objects from whole slide images of a single patient tissue, according to exemplary embodiments of the subject disclosure.
Figure 3B:
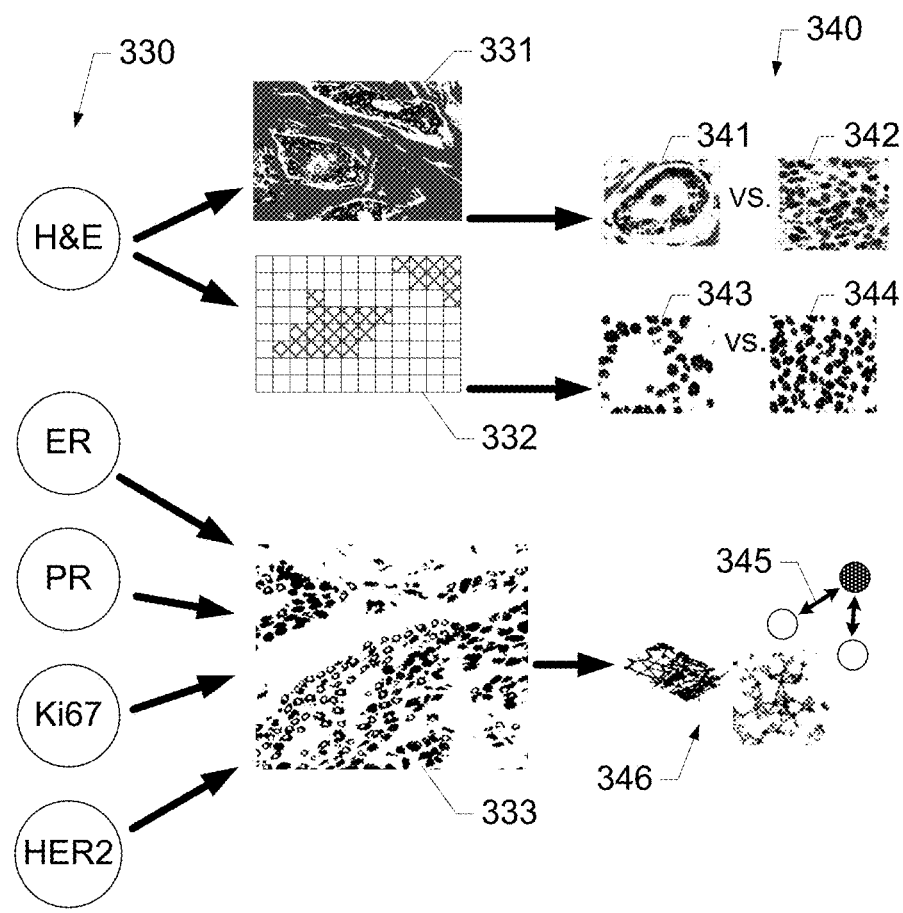
Figure 3C:
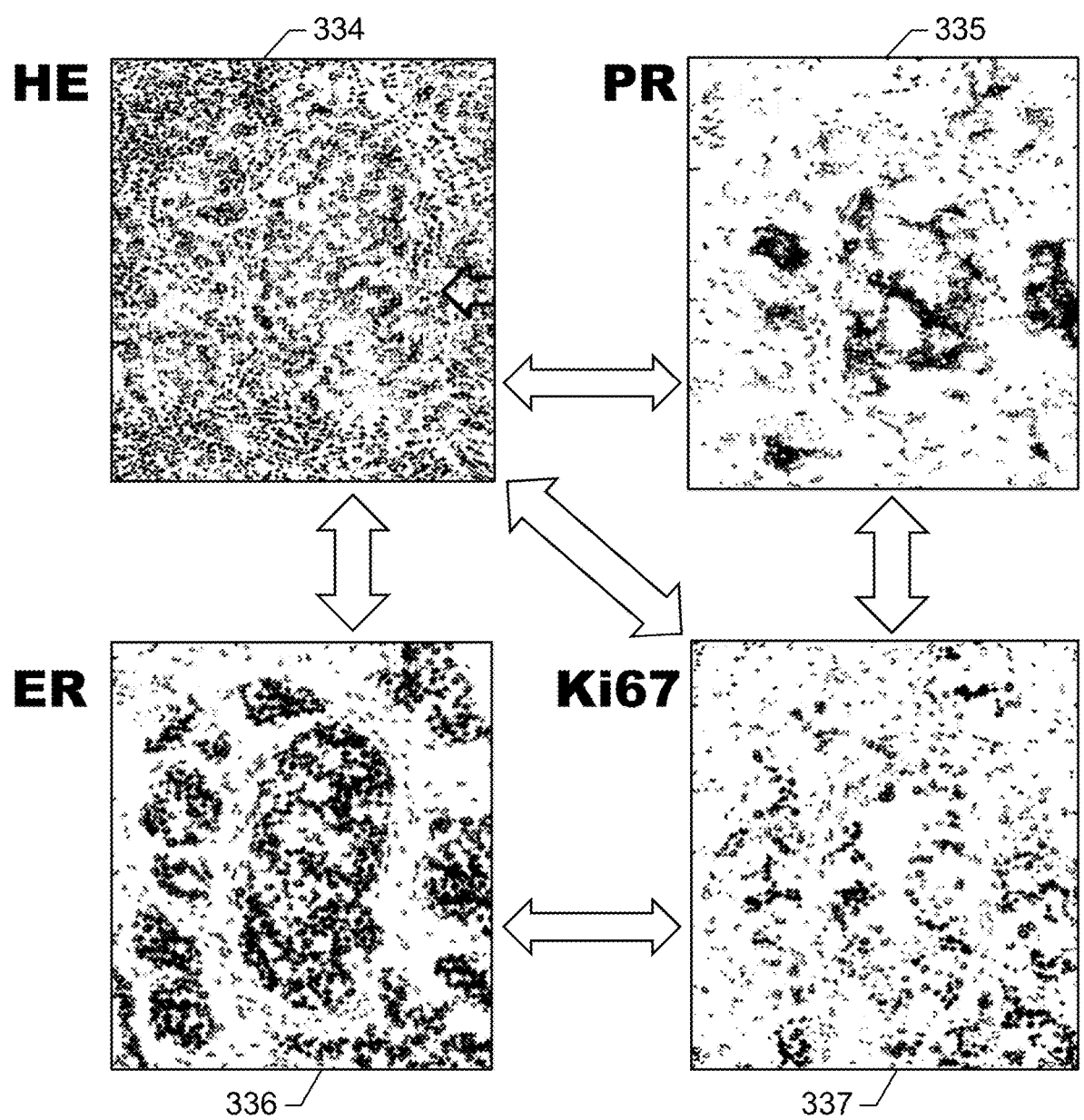

FIGS. 3A-3C depict methods for feature list generation, according to exemplary embodiments of the subject disclosure. The operations described in this exemplary method may use components described with reference to system 200, or other components that perform similar functions. For example, an imaging input may digitize or scan whole-slide images corresponding to serial sections of a tissue sample from a human patient. The image input may include any means for receiving an image of a tissue specimen mounted on a slide, such as a staining and/or imaging platform. Slide images may be received (S301) from said image input via a network, or any other communications means. For training purposes, the images may include a training cohort that consists of a set of immuno-histopathology tissue slides from multiple patients along with their clinical outcome data. Either whole slides can be digitized using a whole slide scanner at the desired magnification of 20/40× or a pathologist can review the slide under a digital microscope and select regions for image analysis and capture only those regions. Therefore, fields of view may be selected (S302), such as a whole-tumor section or specific sections, and registered using registration algorithms as described above. Moreover the same method is applicable independent of whether the annotations are from whole tumor annotations or FoV annotations.

Upon designating a field of view (S302) and/or registering the field of view across images, the individual marker slides may be analyzed (S303) to detect and classify the various tissue objects, such as cells, glands and tissue regions. These operations include, for instance, counting the number of tumor cells in a hematoxylin channel that is unmixed or deconvolved from the RGB whole-slide image. A region of an image or an entire image (e.g., a digital whole-slide image) may be analyzed based at least in part on information and characteristics associated with the whole slide and features selected for quantitative analysis. Cellular structures (e.g., nuclear objects, nuclei seed) and cells in a region of a slide (e.g., a particular tissue region of the slide) or the whole slide may be identified based at least in part on information pertaining to data associated with tissue containing regions of the slide.

In addition to detecting and classifying objects (S303), various types of local and global features of these cells may be computed (S304) to identify the cell types and perform quantitative analysis. The feature computation (S304) can use information from not only an annotated region or FOV of a slide but also information from the whole slide (e.g., tissue-containing regions of the slide analyzed at multiple magnifications). This analysis may be marker-slide specific, as described above. The captured image information and the detected tissue objects may be used to compute object-level features and relational features (S305) in each marker slide. Marker-specific biological features may comprise local shape features computed for the detected nuclei in an ER slide, for instance, may include shape features such as area, eccentricity, perimeter, orientation etc., and image intensity features include the average stain intensity for the nucleus, the intensity variation within a nucleus etc.

Further, sets of relational features computed (S305) between the detected nuclei, glands, and regions, may include an average distance between any two tumor nuclei, or the distance of nucleus to the nearest epithelial region and the distance of a stromal cell to the nearest tumor region, the nearest distance of a tumor nucleus to a lymphocyte cell, the local density of lymphocytes, the local density of tumor nuclei, etc. These and other features identified by the analysis modules are listed in Table 1.

Subsequently, a slide-level feature analysis (S306) operation is executed to compute aggregate slide-level features from the object-level and relational features. For each of the object-level feature type computed for each marker, a histogram of the feature values from all the detected tissue objects in the analyzed image is constructed. For each of these features, simple summarizing metrics including but not limited to: average, mode, standard deviation, minimum and maximum values may be computed. A representative set of these marker specific slide-level features is also listed in Table 1. Based on the slide-level features computed for each marker, one or more inter-marker co-expression features may be identified and computed (S307). Representative inter-marker features are also listed in Table 1.

Subsequently, a case-level feature vector is computed (S308) for the patient. This includes computing aggregate case-level features for a slide or plurality of slides associated with a patient or a case, and concatenating the slide-level features computed for each of the individual markers and inter-marker co-expression features to construct a case-level feature vector for the patient. For example, a patient risk category label from all the training set patients is concatenated as a single column vector, i.e., the ground truth vector. Thus, an element in the ground truth vector corresponds to the category label of a single patient. The row index of a patient's feature vector in the feature vector is the same as the element index of the patient's category label in the ground truth vector. This relation ensures that a patient's image-feature data is correctly associated with the particular patient's risk category label information. The elements of a single row in the feature matrix correspond to all the features, i.e. case-level feature vector information, from one single patient. The elements in a single column correspond to the values of that particular feature from all the patients. For example, a feature matrix may comprise an N×M matrix, with N number of patients under observation, and M number of features. An exemplary set of all the features listed in Table 1 may collectively constitute case-level features for a patient.

Referring now to FIG. 3B, a plurality of IHC training images 330 including an H&E slide, ER, PR, Ki67, and HER2 are processed by image analysis algorithms to detect structures and features thereof. As regards marker-specific biological features, for instance, from the H&E slide, lymphocytes and tumor nuclei are detected, and within the IHC slides, nuclei detection is used to classify nuclei as positive and negative. Image analysis methods to detect nuclei objects methods may be used to detect lymphocytes and tumor nuclei 331 from the H&E slide; similarly, H&E slides may also be subject to superpixel segmentation/region segmentation to identify tumor and stromal regions, as depicted in superpixel image 332. Similarly, positive and negative nuclei are identified from the IHC slides ER, PR, Ki67, and HER2 in image 333. Then, the respective marker-specific biological features are computed, such as morphological features such as nuclei, tumor structures, etc, e.g. in images 341 vs 342 computed from the H&E slide for acquisition of the respective feature. Nuclei and glandular features such as size, shape, density, etc. are also computed, such as in images 343 vs. 344. Relational and contextual features 345 such as distances and features within neighborhoods are computed.

Similar processes for relating across marker slides 346 are used to determine distances and relations between detected objects on different slides, such as clusters of objects, co-occurrence of objects, etc. Based on feature values computed for single tissue objects, for each of the features, the heterogeneity of the feature on the slide is computed from the feature values from all the tissue objects.

FIG. 3C shows a tumor region shown in an H&E image 334 with high (homogeneous) estrogen expression while, in a PR image 335, the expression is not homogenous but heterogeneous. The Ki67 image 337 depicts a proliferation marker and shows different expressions of these features. This type of comparison across IHC slides enables a gland-level or regional-level correlation that can be linked with clinical outcome based on the machine learning. In other words, a plurality of inter-marker features is computed, whereby each one of the inter-marker features is obtained by calculating a feature specific combination of the numerical values of pairs of the marker-specific biological features acquired from different ones of the images. Instead of a pair, the combination can be obtained for a larger number of the marker-specific biological features acquired from different ones of the images. The combination can be an elementary or complex mathematical operation or algorithm, such as a multiplication of feature values or calculating a correlation coefficient that provides a local relation of the marker-specific biological features. Each pair or tuple of marker-specific biological features and each permutation thereof may be used to calculate a number of different combinations using various mathematical algorithms such that a large number, e.g. several thousand, inter-marker features result.

This allows a data mining for granular features to determine implicit relations between glands and regions and clinical outcome, which are generally not quantified or used in traditional slide-level scoring methods percent positivity and H-score. The data mining provides prognostic features as a sub-set of the original set of marker-specific biological features and inter-marker features that are most useful for cancer risk prediction. The data mining may be performed by L1-regularized logistic regression.

Figure 4:
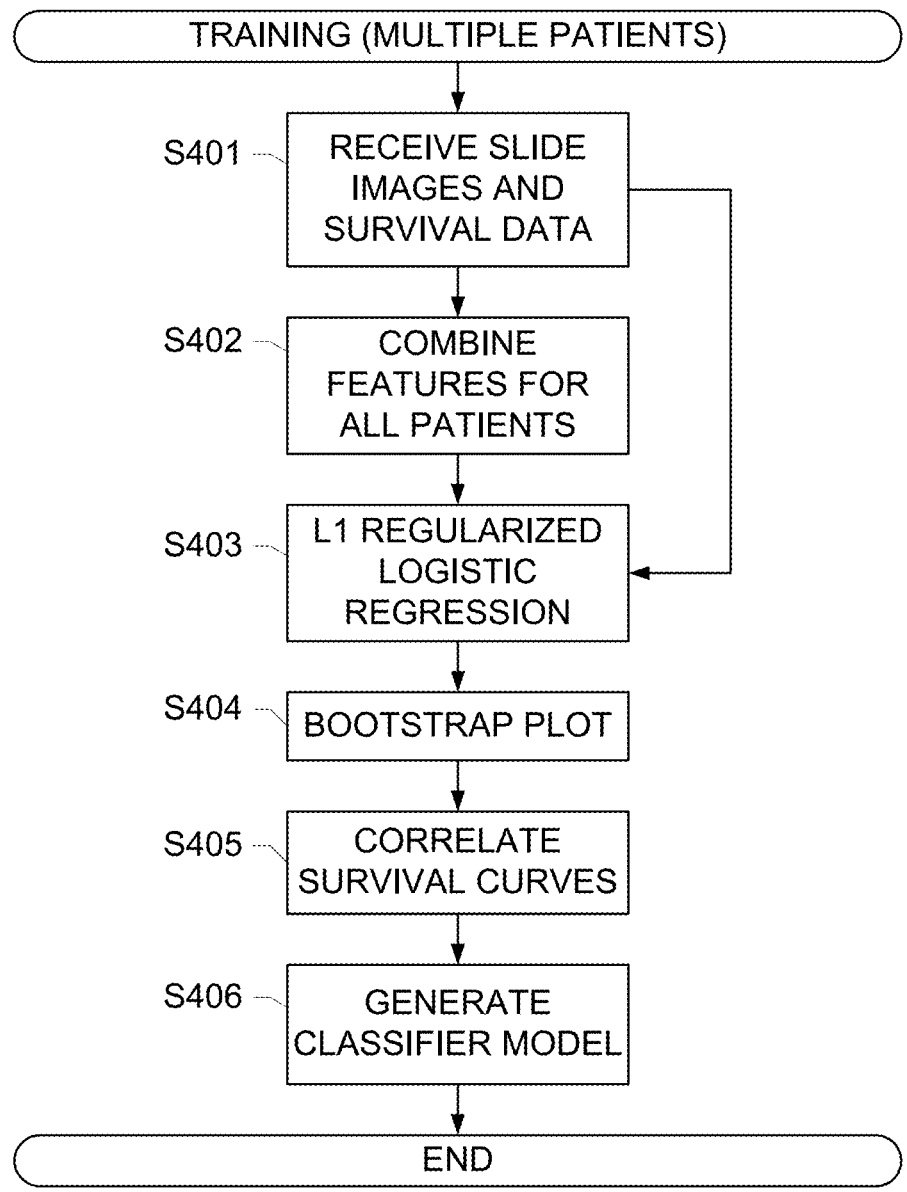
FIG. 4 depicts a method for aggregating feature information from all the patients in training cohort and training a machine learning classifier to assess the risk of recurrence, according to an exemplary embodiment of the subject disclosure.

FIG. 4 depicts a method for training a classifier, according to an exemplary embodiment of the subject disclosure. As described herein, a machine-learning-based binary classifier may be trained using a feature matrix generated from the case-level features for a plurality of patients in a training set. The feature matrix constitutes the feature information gathered from all the patients' slides, along with clinical outcome data for each patient in the training set. Each patient may be categorized to be belonging to a low-risk group or a high-risk group. The patient category label information is considered as the ground truth for the classifier along with the survival data that is received (S401) by the training module for training the classifier and building a prognostic model that may be subsequently used to classify a new data sample. The features for all the patients are combined (S402) into a feature matrix as described herein, and input into an L1 regularized logistic regression operation (S403). The L1 regularized logistic regression is suitable classifier approach, given the several (thousand) features relative to the few number of samples. Logistic regression is a statistical classification approach which models the conditional posterior probability (the conditional probability of low-risk or high-risk labels, given the features observation values) as an exponential function of the linear weighted sum of the computed features. The weights constitute the model parameters and are estimated from the given training set. Thus, the classifier design, i.e. posterior probability model parameter estimation, amounts to the estimation of the unknown weights from the training cohort and the resultant binary classifier is a linear classifier. L1-regularized logistic regression is a recently developed method built upon the traditional logistic regression method, in addition to estimating model parameters, to also systematically select a subset of discriminating features, i.e. feature (variable) selection for classification. In statistical literature, such methods are referred to as "Shrinkage" or "Lasso" methods, cf. Efficient L1 Regularized Logistic Regression, Su-In Lee, Honglak Lee et. al., Computer Science Department, Stanford University http://web.eecs.umich.edu/~honglak/aaai06_L1logreg.pdf. Given training data, model fitting and parameter estimation of the parameters is numerical non-linear optimization problem. For efficient model fitting and estimating the model parameters, exemplary embodiments of the subject disclosure utilize the L1-regularized logistic regression implemented in the glmnet package (http://cran.r-project.org/web/packages/glmnet/glmnet.pdf) in the R programming language to perform simultaneous feature selection and parameter estimation.

To evaluate and validate the prognostic model performance, multiple statistical procedures such as cross validation, bootstrap analysis (S404), AUC performance, and survival analysis are used. In order to assess the robustness of the model and the relative importance of each prognostic feature/variable, a bootstrap analysis (S404), samples with replacement from the true dataset 100 times, fitting the model, and recording how many times each feature is included. This include, for example, validating that the estimated classifier model is generalizable and performs equally well on any independent new test dataset and is not "overfitting" to the training set alone, using a leave-out-one cross-validation (LOOCV) approach. Leave-out-one cross validation (LOOCV) is a widely used statistical method to estimate the model prediction error. Further, using the predictive error computed using cross validation, the ROC (receiver operating curves) are generated. In the generated ROC curve, the area under curve (AUC) is computed to quantitatively evaluate the classifier performance.

Additionally, once the prognostic model is estimated based on the recurrence time, which are derived from the given clinical outcome information for both the low-risk and high-risk groups as categorized by the prognostic model, standard Kaplan-Meier survival curves are estimated and output in a correlation operation (S405). Once the correlation (S405) provides a reliable output that matches the known survival curves of the patients in the training dataset, the resulting classifier model is generated (S406) and used for reliable subsequent testing.

To facilitate the construction of the feature matrix that is input to the classifier, in each patient tissue slide, for each of the detected tissue objects, several features may be computed as mentioned below. The granular tissue object is a nucleus blob. A nucleus blob is a group of connected pixels around the identified nucleus center/seed, which represents the nucleus. The nucleus blob can represent either a positively stained tumor nucleus, negatively stained nucleus, stromal cell, lymphocyte or a pixel group falsely identified as a nucleus. The low-level features to quantify size and shape in different ways are computed to differentiate between different types of cells. The different features that have been used are as follows:

Nucleus Blob Shape Based Features:

Based on the nucleus blob mask detected around a seed point, the blob shape is approximated by an ellipse. The minor axis of the ellipse is used as a feature along with the eccentricity parameter (computed as the ratio of minor axis to major axis). The rationale behind using the shape based feature is that the stromal cells are more elongated than negative cells and lymphocytes. Hence, it is expected that eccentricity will be lower for stromal cells; also, the minor axis parameter of stromal and lymphocytes are generally lower than that of the negative cells.

Nucleus Area Feature:

The size of the blob, in terms of the number of pixels, is also used as a feature. The size of stromal cells and lymphocytes are generally smaller than that of the negative cells.

Blob Compactness Features:

Considering a circular region centered at the blob center which has the same area as the blob, the area of the overlapped region between this circular region and the blob is called "overlap area", the compactness feature of the blob is then computed as: Compactness=Overlap Area/Blob Area. This feature is used to differentiating irregular and non-nuclei shapes from nucleus.

Blob Density Features:

These features are expected to be highly discriminatory for lymphocytes versus stromal and negatives. For lymphocytes, the cells are more closely packed than for negatives and stromal cells. Also, for lymphocytes, the average blob size is lower than that of negatives. Hence, a density based feature is used which accounts for both the packing density of the nearby seeds and the distribution of the neighborhood blob sizes. The features are computed using a window of size (2*radius+1)×(2*radius+1) around a given seed for multiple values of radii, in our implementation ranging from 5 um to 25 um. For each radius value, the following features are computed:

Blob Pixel density, Blob Seed Density, Normalized pixel density(normalized with average size of the nucleus blob), Normalized Seed density feature.

Normalized Color Feature:

For each blob, the normalized red and blue colors are considered. For a pixel valued (R, G, B), the normalized red color RN=R/(R+G+B), and the normalized blue color BN=B/(R+G+B). In IHC images, the positively stained tumor cells appear as DAB brown colored blobs whereas the hematoxylin blue stained negative tumor cells, lymphocytes and stromal cells appear as blue blobs. The mean and standard deviation of the RN and BN channels for all the pixels inside the blob are computed. The normalization is done so as to account for data variability, where different slides can vary in brightness and contrast (and hence, in absolute R, G and B values).

PC1 ratio: This feature accounts for the blue and brown blob appearance variability of the individual nuclei in IHC slides. Principal component analysis (PCA) is done and the projection of the RGB image along the first principal component vector (PC1) is taken. For a given seed, a weighted covariance matrix is constructed using the row and column indices of the pixels inside the blob and the weighting factor depends on the PC1 value at the pixel locations. After singular value decomposition, the ratio of the maximum eigenvalue to the minimum eigenvalue is considered as the PC1 ratio feature. For stroma, the blob pixels are distributed in a more elongated way than in negatives and lymphocytes, where the pixels are distributed in a more circular manner. Hence, maximum and minimum eigenvalues are more similar for negatives and lymphocytes than for stroma; i.e. PC1 ratio is higher for stroma, than for negatives and lymphocytes.

The same feature is also obtained from the hematoxylin component image which better represents the stroma, lymphocytes and negative cells.

Combined eccentricity: this feature equals (PC1 ratio)/(eccentricity of ellipse). PC1 ratio is higher for stroma and eccentricity is lower for stroma, than for negatives and lymphocytes; hence this feature is expected to be more discriminatory for stroma. The same feature is also computed using PC1 ratio obtained from HTX component images.

Combined ellipse feature: this feature equals (minor axis of ellipse)×(eccentricity of ellipse). For stroma, both the minor axis and eccentricity are lower as compared to negatives; hence this feature is more discriminative for stroma.

Absolute Color Features:

Apart from the normalized color channels, the mean of the R, G and B channels are considered for the pixels inside the blob. This color feature helps to distinguish positive cells from negatives, lymphocytes and stroma.

Nearest Neighbor (NN) Features:

This feature is similar to the blob density feature and it considers the distribution of the seeds within a given window around the seed (it does not consider the blob sizes). A window of size (2*50+1)×(2*50+1) is considered around the given seed. For a given seed, 4 features are computed as follows:

NN feature 1=number of seeds inside the given window around the seed considered

NN feature 2=mean of the (distance of the seeds inside the window from the given seed)

NN feature 3=NN feature 1−median(NN feature 1 for all the seeds in the FOV)

NN feature 4=NN feature 2−median(NN feature 2 for all the seeds in the FOV)

Since the cells are more closely packed for lymphocytes than for stromal and negatives, this feature is expected to distinguish lymphocytes from stromal and negatives.

Lab Feature:

LAB is a well-known color representation of the RGB pixel value, where L represents the pixel intensity and A and B reflect the color. The average of the L, A and B channel values are computed from the averaged value of R, G, B values of all the pixels inside a given blob. Also, the hue is computed as tan-1(average B/average A) as the 4th color feature using the LAB space for a given blob. This color discriminative feature is useful for brown (positives) versus blue (negatives, lymphocytes and stroma) classification.

Nuclei Center Vote strength: the process of finding nuclei centers also outputs a vote strength per every nucleus seed point. This score is expected to be higher at the proper and well-formed elliptical blobs and lower for non-blobby false positives or seeds.

Annular Region Based Features:

Given a blob, a slightly morphologically dilated version of the blob is considered and the difference between the dilated blob and the actual blob returns an annular region. It is expected that for proper blobs, there should be more foreground to background separation and hence, the annular region will be much discriminative form the foreground.

Annular region based features on the Y and blue channels, where Y indicates the black and white gray scale image computed from the RGB input images.

Annular feature 1=(1+Y_meanouter−Y_meaninner)/((Y_meaninner)*(0.01+Y_stdinner))

Annular feature 2=(1+Y_meanouter−Y_meaninner)/((Y_meaninner)*(0.01+Y_stdinner*Y_stdinner)), where Y_meaninner=mean of the Y pixel values inside the blob Y_meanouter=mean of the Y pixel values inside the annular region around a blob Y_stdinner=standard deviation of the Y pixel values inside the blob Similarly, Annular feature 3=(blue_meaninner−blue_meanouter)/((1−blue_meaninner)*(0.01+blue_stdinner))

Annular feature 4=(blue_meaninner−blue_meanouter)/((1−blue_meaninner)*(0.01+blue_stdinner*blue_stdinner)), where blue_meaninner=mean of the blue pixel values inside the blob blue_meanouter=mean of the blue pixel values inside the annular region around a blob blue_stdinner=standard deviation of the blue pixel values inside the blob.

Considering the HTX (hematoxylin) component image and DAB component image, the following annular region based features are computed:

HTX_meaninner=mean of the pixel values inside the blob from HTX component image, HTX_meanouter=mean of the pixel values inside the annular region around a blob from HTX component image, HTX_stdinner=standard deviation of the pixel values inside the blob from HTX component image, DAB_meaninner=mean of the pixel values inside the blob from DAB component image, DAB_meanouter=mean of the pixel values inside the annular region around a blob from DABcomponent image, and DAB_stdinner=standard deviation of the pixel values inside the blob from DAB component image.

It is expected that for blue cells, the interior of the cell is more blue than the annular region; hence blue_meaninner>blue_meanouter is expected. For brown cells, the interior is expected to be darker than the annular region. Hence, Y_meanouter>Y_meaninner is expected (in the Y channel, "dark" and "bright" regions corresponds to lower and higher pixel values, respectively). The features are normalized using the standard deviation or the variance of pixel values so as to be more robust to noisy pixel values inside the blob. The annular features are expected to distinguish brown cells from blue cells and differentiate proper cells from false detections.

Blob Topography Features:

Consider a blob as a 3D object with the pixels value in the Z dimension, the topography features are to describe how "flat" (or "dome-shaped") the blob is in the HTX component image. These include the DoH (determinant of Hessian) feature and the DoG (difference of Gaussian) feature.

In mathematics, the Hessian matrix is a square matrix of second-order partial derivatives of a function. For 2D image, the Hessian matrix has size 2×2, and the partial derivatives can be computed using 3×3 Sobel filters in the X and Y directions, respectively. The determinant of the Hessian matrix is computed for each pixel within the blob. Then the maximal and the mean DoH values in the blob are computed as the feature. It is expected that the lymphocytes usually have higher DoH feature value than the negatives.

The DoG image is obtained by subtracting one blurred version of an original image from another less blurred version of the original. The blurred images are obtained by convolving the original image with Gaussian kernels having differing standard deviations. Two levels of DoG images are obtained using 3 Gaussian kernels, with the first level mainly responding to larger blobs, and the second level responding to smaller blobs. Again, the maximal and mean DoG values in each blob are computed as the feature. It is expected that lymphocytes and negatives have different responses in each level of DoG image. Jointly using multilevel DoG images can help differentiating these two types of cells.

"Reference blob size" feature is the median size of all the positively stained DAB brown blobs in IHC images. As the positive and negative cancer cells should have similar sizes, the median size of the brown blobs is also a good estimate of the negative cells size within that FOV. In case there are no brown blobs identified, the Otsu thresholding is applied on the size of all the round blue blobs, and the Otsu threshold is used as the reference blob size feature.

"Reference HTX" feature is the median HTX_meaninner of all the round blue blobs whose size is greater than the reference blob size, which is a good estimate of the HTX_meaninner value of negatives within that FOV.

Similarly, "Reference DoH", "Reference Y(Intensity)", "Reference A" and "Reference B" features are also obtained for the DoH, intensity and A, B features from the round blue blobs whose size is greater than the reference blob size.

In case no brown blob or round blue blobs are identified, all the reference features are set to zero except for reference A and reference B, which are set to the median A and median B of all the negatives from the training data.

"Difference from reference blob size" is the difference between the blob size and the reference blob size, which describes if a blob is "large" or "small" when comparing to the estimated size of negative cells in the FOV.

"Difference from reference HTX" is the difference between the HTX_meaninner and the reference HTX, which describes if a blob stain is "strong" or "faint" when comparing to the estimated HTX stain strength of negative cells in the FOV.

"Difference from reference DoH" is the difference between the mean DoH and the reference DoH, which describes how "flat" a blob is when comparing to the estimated negative cells in the FOV.

"Difference from reference A" and "Difference from reference B" describe the color difference of a blob when compared to the estimated negative cells in the FOV.

"Adjusted mean DoH" is the score generated by a linear SVM classifier pre-trained on negatives and lymphocytes using the "mean DoH" and "HTX_meaninner" features. It can be considered as the mean DoH feature adjusted according to the HTX stain strengthens. Since stronger stain tends to yield higher mean DoH value compare to fainter stain, "Adjusted mean DoH" is intended to reduce the impact caused by the stain variations cross different FOVs (or slides).

"Number of small neighbors" is the number of blue blobs whose size is smaller than "0.6× reference blob size" within a circular neighborhood around each seed. It is expected that number of small neighbors is greater for lymphocytes than for negatives.

"Number of large neighbors" is the number of blue blobs whose size is greater than "0.6× reference blob size" within a circular neighborhood around each seed. It is expected that number of large neighbors is greater for negatives than for lymphocytes.

Aggregating the features computed for the individual tissue objects, various summary statistics of the nuclear level features such as mean, interquartile range, standard deviation (heterogeneity) etc. may be computed for different cell types.

Spatial relationship features within each stain: the average minimum distance between cells of each type, e.g. the average distance between ER positive cells and lymphocytes, and the Clark-Evans aggregation statistic to measure how clustered positively staining nuclei are.

Co-occurrence features are computed across multiple registered images. After registering the images from different stains, all possible inter-marker co-occurrence statistics are calculated, e.g. the average number of ER positive nuclei within 30 um of a Ki67 positive nucleus which provides a spatial correlation coefficient.

Table 1 shows some exemplary feature labels and their description, with the assumption that those having ordinary skill in the art can vary the details without departing from the novel scope and spirit gleaned from reading this disclosure. In this embodiment, an overall set of 525 image features existing on diverse scales is calculated, both continuous and discrete. For example, ER_pos2pos can be changed to PR_pos2pos, to correspond to a similar feature within a PR-stained image and similarly Ki67_pos2pos within a Ki67-stained image.

TABLE 1

EXEMPLARY FEATURE LIST

| Feature | Description |
| --- | --- |
| Lymphocyte Count | Total count of lymphocytes in the whole slide within a spatial neighborhood (in our embodiment, a dilated extent of of 100 um around the tumor regions. The lymphocytes are detected and counted in H&E whole slide. |
| TumorRegionProp | Proportion of the Area of tumor region in the H&E tissue slide |
| StromaRegionProp | Proportion of the area of the stromal region detected in the H&E tissue slide. |
| ERCellTypeProp, PRCellTypeProp Ki67CellTypeProp HER2CellTypeProp | Proportion of particular cell type (Positive, Negative, Stromal, Lymphocytes) in the particular marker staining cells out of all the detected cells for each stain. |
| ERPercentPos, PRPercentPos, Ki67PercentPos | Percentage of marker positive tumor cells amongst all the tumor cells detected. Total number of tumor cells = Positive + Negative stained tumor cells. |
| ER_pos2pos, ER_neg2pos, ER_stroma2pos, ER_pos2neg, ER_neg2neg, ER_stroma2neg, ER_pos2stroma, ER_neg2stroma, ER_stroma2stroma | Average minimum distance difference from cell type 1 to cell type 2. pos = positively staining tumor cells, neg = negatively staining tumor cells, stroma = stromal cells. For example, neg2pos is calculated by finding the closest positive cell to every negative, and averaging the distance between them. This is intended to give information about the heterogeneity, co-occurence and spatial organisation of the different cell types. Similar to average statistic, other population statistics such as median, standard deviation, minimum, maximum, interquartile range are also included in the feature list. |
| ER_MinorAxisLength | Width of cell at narrowest diameter. |
| ER_AxisRatio | Measure of eccentricity. |
| ER_TumorCell Size Heterogeneity | Variation in the size of all the tumor cells detected in the whole slide. Computed for all the different IHC markers and cell types. |
| ER_Intensity Heterogeneity | Heterogeneity of the ER positive stain intensity amongst all the ER positive stained tumor cells. |
| ER_nonGT_area, ER_nonGT_ratio, ER_nonGT_pow | Area of cell, ratio of cell area over median area of all cells, and 10^ratio of cell area over median area of all cells. |
| ER_blob_density(1 ... n) | Image density at increasing radii. |
| ER_meanValNormalizedRed, ER_stdDevValNormalizedRed, ER_meanValNormalizedBlue, ER_stdDevValNormalizedBlue, | Mean and standard deviation of the normalized red and blue channels, respectively. |
| ER_meanValRedCh, ER_meanValGreenCh, ER_meanValBlueCh | Mean values of red, green, and blue channels, respectively. |
| ER_PC1Ratio | Principal component 1 (PC1) ratio computed based on covariance matrix computed from mask image ON pixels. |
| ER_PC1eccentricity | Average PC1Ratio/Axis ratio. |
| ER_f1timesf2 | MinorAxisLength × AxisRatio |
| ER_AxisRatio | Average Ratio of the Major to Minor Axis. |
| ER_iqr_AxisRatio | Interquartile range of the Major to Minor axis ratio. |
| ER_Annulus1, ER_Annulus2, | Standardized blue and Y ratios and variance |

TABLE 1-continued

EXEMPLARY FEATURE LIST

| Feature | Description |
| --- | --- |
| ER_Annulus3, ER_Annulus4 | thereof, respectively. |
| ER_M2_CoExpression | Co-expression of ER and Marker2 stained cells in the adjacent slide. Proportion of Marker2 stained cells within the ER positive stained tumor region. Marker2 can be any of the other three markers (PR, Ki67 and HER2). |

Figure 5A:
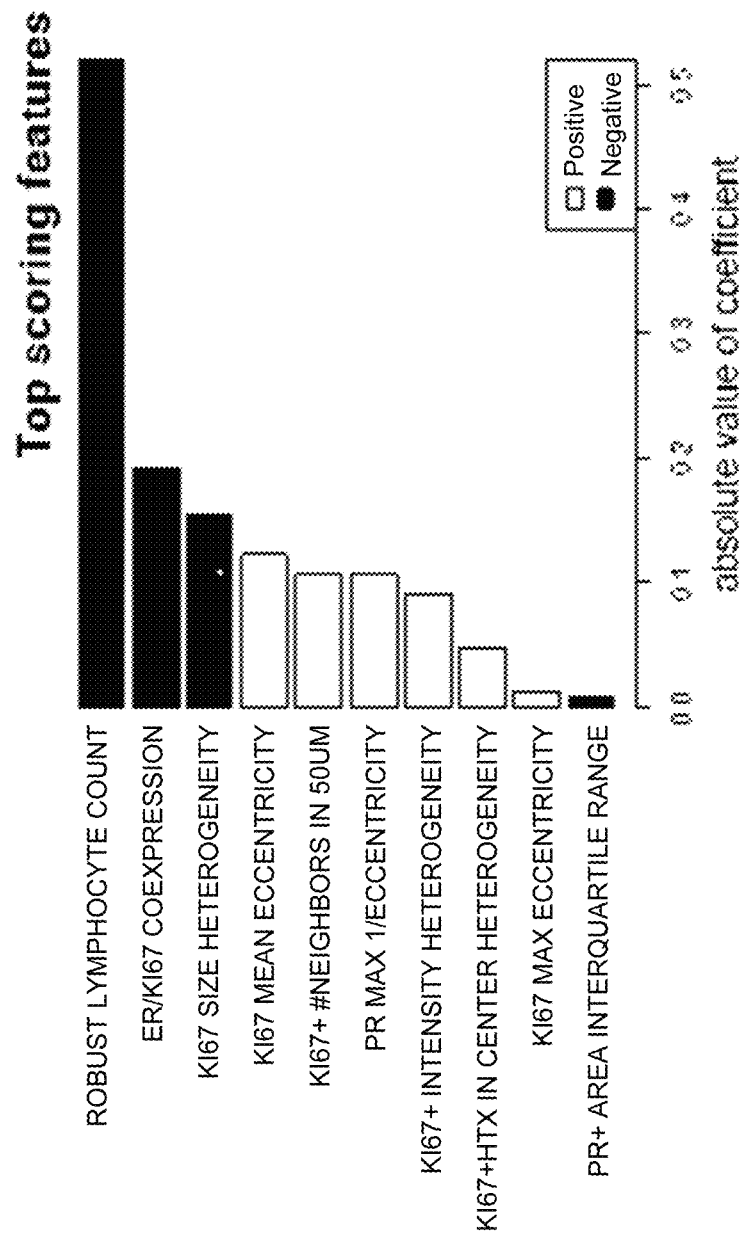
FIGS. 5A-5C depict optimal and relevant prognostic features and their correlative analysis and validation, according to exemplary embodiments of the subject disclosure.
Figure 5B:
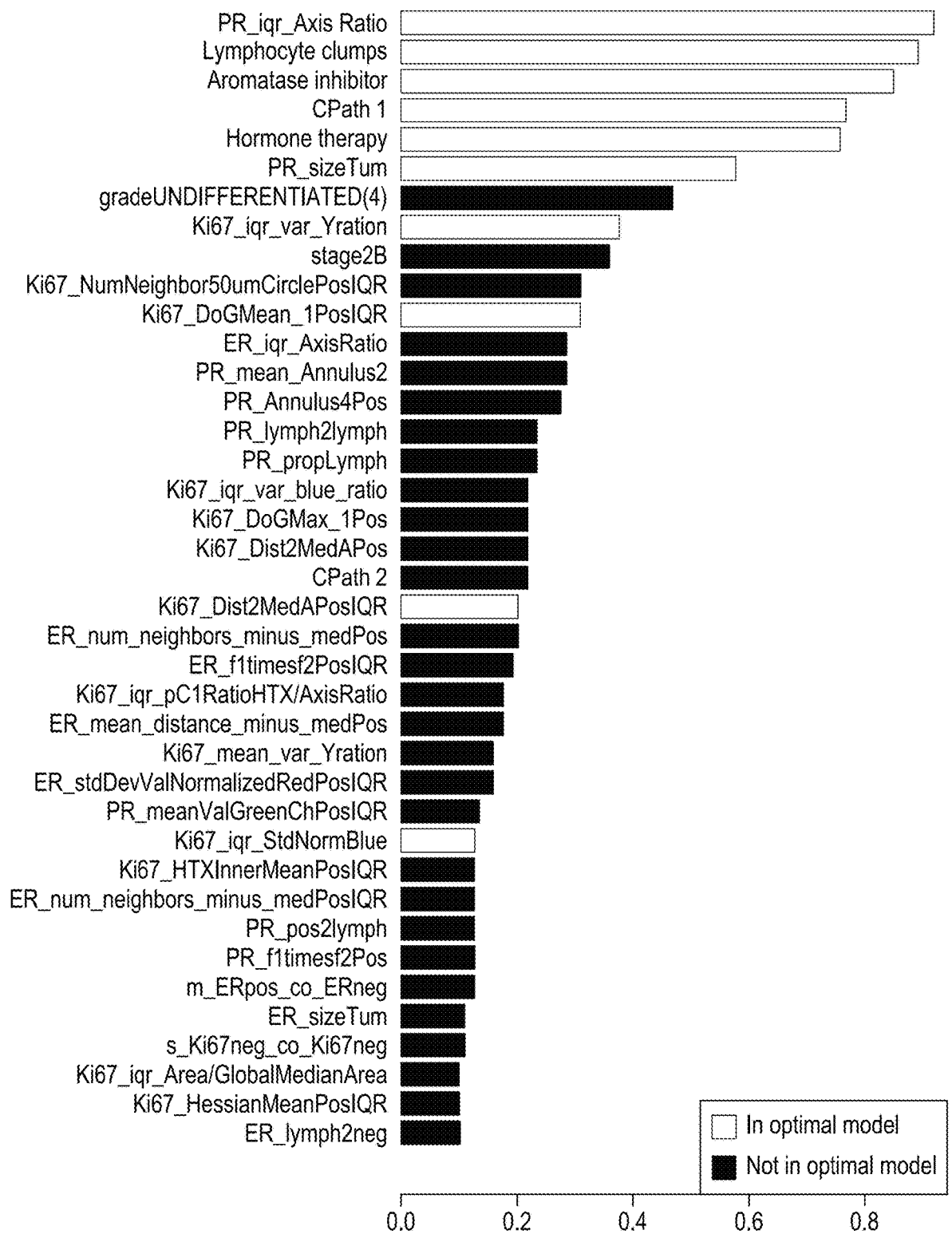
Figure 5C:
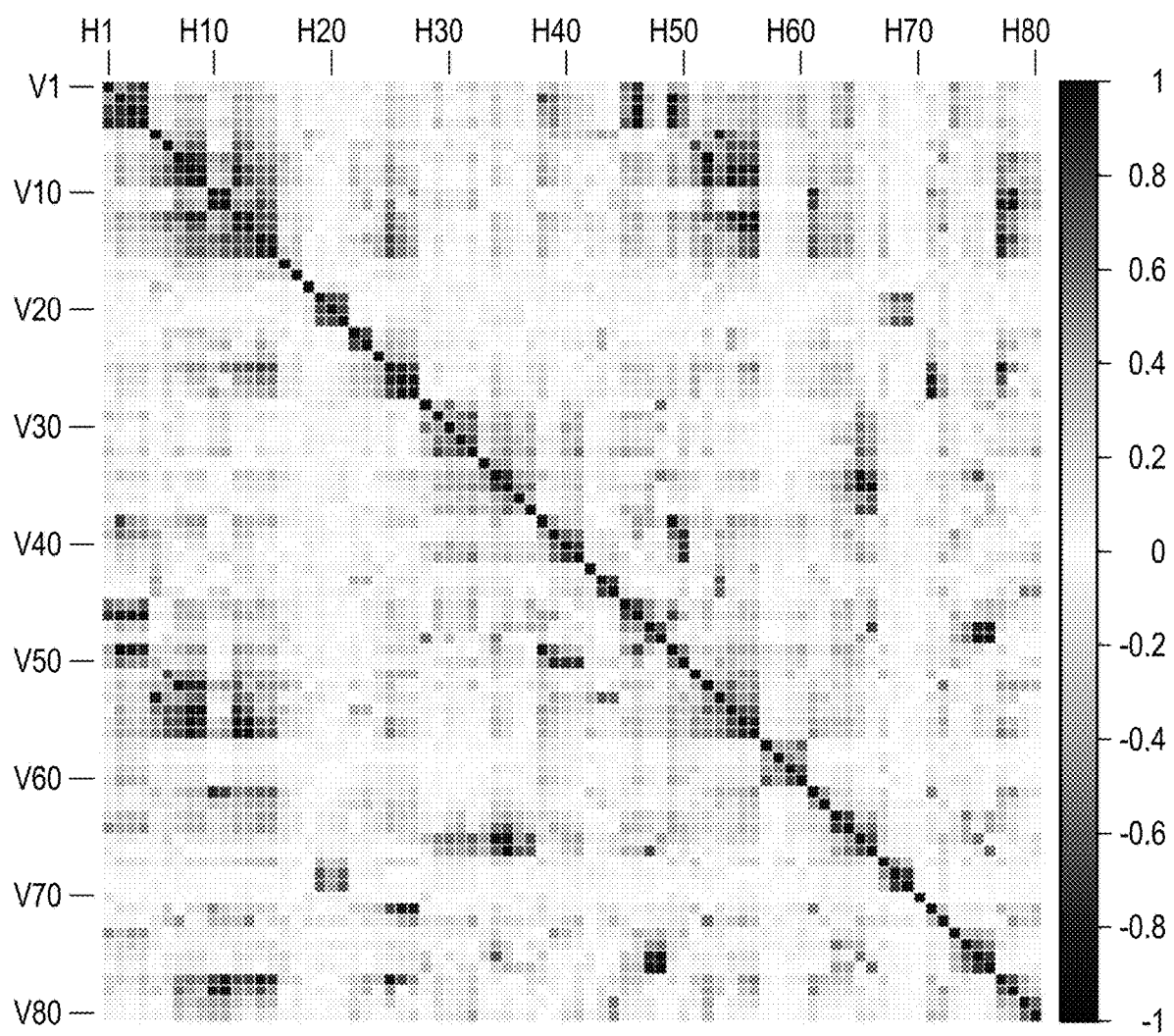

FIGS. 5A-5C respectively show optimal features that are selected and output by L1-regularized logistic regression module and correlations thereof, according to exemplary embodiments of the subject disclosure to provide the prognostic features. FIG. 5A shows a list of the optimal features input into a model for any recurrence, according to an exemplary embodiment of the subject disclosure. For the training cohort that is used in this embodiment, top prognostic features are listed below. With variations to the training cohort, either by including or excluding patient samples or on a completely varied training cohort the prognostic variables and the associated parameters may vary. The list of resultant prognostic features are explained below in Table 2:

TABLE 2

TOP PROGNOSTIC FEATURES

| | |
| --- | --- |
| Lymphocyte Count | Count of Lymphocytes in the vicinity of the tumor region. |
| ER_Ki67_Coexpression | Proportion of Ki67 stained tumor region within the ER stained tumor region. |
| Ki67 Size Heterogeneity | Size variation of Ki67 positive tumor cells. |
| Ki67 Mean Eccentricity | Average Eccentricity of Ki67 positive tumor blobs. |
| Ki67 Density within 50 um | Average Density of Ki67+ neighbors within a 50 um radius around cell Ki67+ cell. |
| Ki67+ Intensity Heterogeneity | Heterogeneity of Ki67+ staining intensity. |
| Ki67+ HTX Heterogeneity | Heterogeneity of Hemotoxylin stain intensity within Ki67+ tumor cells. This features indicates the staining variability with aggressive tumor cells. |
| PR+ Area IQR | Interquartile range of the PR+ tumor cell size. Indicative of the tumor cell size variations. |

As illustrated above, dominant prognostic features were reflective of the Ki67, proliferative marker, overexpression, co-expression of Ki67 and ER markers, the density and count of the lymphocytes in the vicinity of tumor region (peri-tumoral region) and the tumor cell size, shape and intensity heterogeneity. The prognostic features were selected by the machine learning algorithm from the exhaustive set of features that were input to the machine learning module by correlating the feature data against the low and high-risk recurrence training information.

This list of prognostic features is subject to bootstrapping and correlation as described above, and a list of features for the optimal model is generated and depicted in FIG. 5B. FIG. 5C shows a correlation of features computed for each cell or structure and aggregated in a slide, or between two different marker slides. The slides may be from the same patient, or from different patients. Correlations between features may be determined by indexing the features in rows and columns. A negative correlation is a zero value, a positive correlation is a 1 value. This is one of several examples of depicting the results of the data-driven approaches described herein.

Figure 6:
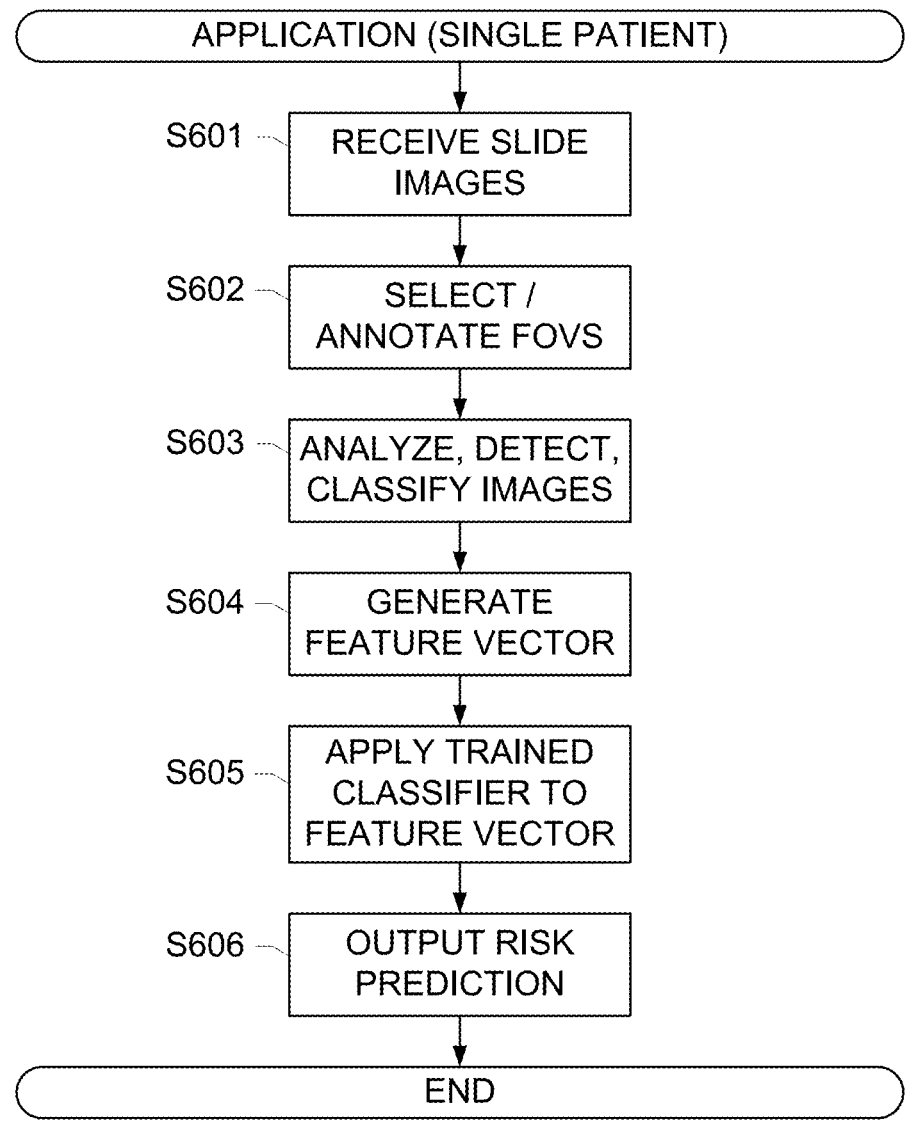
FIG. 6 depicts a method for assessing a risk of cancer recurrence for a new patient using the trained prognostic model, according to an exemplary embodiment of the subject disclosure.

FIG. 6 depicts a workflow and method for assessing a risk of cancer recurrence for a patient using the trained classifier, according to an exemplary embodiment of the subject disclosure. The patient's H&E and IHC test tissue slides are digitized using the whole slide scanner and received (S601) by, for instance, a module for executing the method. As with the training tissue slides, the regions within the digital images are selected for analysis (S602) either by annotating whole tumor regions or couple of representative fields of view (FOVs). Image analysis algorithms may be used to analyze the images (S603) and detect and classify the various tissue objects as described herein, for instance, with reference to FIG. 3B. For these detected tissue objects, the prognostic image features mentioned above, for example with respect to FIG. 5A, are computed to generate the prognostic feature variable vector (S604) for the patient. Using the prognostic model learnt by the training methods described herein, for example with reference to FIG. 4, step S406, the prognostic feature vector for the patient is linearly weighted by the model parameters estimation and summed, and the logistic function thereof computed, to predict the posterior model probability of the patient belonging to low- and high-risk of recurrence, which is then output (S606) as a respective signal. The signal may be indicative of a requirement for an adjuvant chemotherapy in case of high-risk recurrence or the signal may be indicative of the adjuvant chemotherapy being unnecessary in case of low-risk recurrence.

The operations disclosed herein may be ported into a hardware graphics processing unit (GPU), enabling a multi-threaded parallel implementation. Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices. Examples of input devices include a keyboard, cursor control devices (e.g., a mouse), a microphone, a scanner, and so forth. Examples of output devices include a display device (e.g., a monitor or projector), speakers, a printer, a network card, and so forth. Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device. In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof. A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device. In some embodiments, a computer program product is described comprisvbing a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts. Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution. Also, a computer may include one or more library files, experiment data files, and an internet client stored in system memory. For example, experiment data could include data related to one or more experiments or assays, such as detected signal values, or other values associated with one or more sequencing by synthesis (SBS) experiments or processes. Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

The invention claimed is:

1. A system comprising:
    a processor; and
    a memory coupled to the processor, the memory storing computer-readable instructions that, when executed by the processor, cause the processor to perform operations comprising:
        accessing a plurality of images corresponding to a tissue sample, wherein a first image of the plurality of images is a hematoxylin-and-eosin (H&E) image and a second image of the plurality of images is an individually stained or a multiplex immunohistochemical (IHC) image;
        detecting, for each image of the plurality of images, a plurality of marker-specific features, wherein each marker-specific feature of plurality of the marker-specific features corresponds to a tissue object represented in an image of the plurality of images;
        computing a plurality of inter-marker features, wherein each of the inter-marker features is computed based on a first value derived from a marker-specific feature of the first image and a second value derived from a marker-specific feature of the second image;
        training a breast-cancer recurrence model using the plurality of inter-marker features and a clinical outcome data of a subject associated with the tissue sample; and
        processing another image using the trained breast-cancer recurrence model to estimate a breast-cancer-risk recurrence score; and
        outputting the breast-cancer-risk recurrence score.

2. The system of claim 1, wherein the H&E image comprises an image of the tissue sample that is stained with one or more stains that highlight one or more structures in the tissue sample.

3. The system of claim 1, wherein the H&E image depicts morphological features within the tissue sample.

4. The system of claim 1, wherein said plurality of images corresponds to more than one tissue sample, each tissue sample of the more than one tissue sample being associated with a different subject and clinical outcome data corresponding to the different subject.

5. The system of claim 1, wherein the training the breast-cancer recurrence model further comprises using features from additional tissue samples and clinical outcome data corresponding to each of the additional tissue samples.

6. The system of claim 1, wherein the training the breast-cancer recurrence model comprises using a machine-learning operation.

7. The system of claim 6, wherein the machine-learning operation includes using an L1-regularized logistic regression.

8. The system of claim 1, wherein training the breast-cancer recurrence model comprises performing a bootstrap analysis.

9. The system of claim 1, wherein training the breast-cancer recurrence model further comprise performing a cross-validation of the breast-cancer recurrence model on a subset of the plurality of images.

10. The system of claim 1, wherein the plurality of marker-specific features includes a nucleus blob shape feature, a nucleus blob area feature, a nucleus blob compactness feature, a nucleus blob density feature, a normalized color feature, an absolute color feature, a center vote strength, an annular region based feature, or a blob topography feature.

11. The system of claim 1, wherein the plurality of marker-specific features and the plurality of inter-marker features includes a count of lymphocytes in a vicinity of a tumor region, a proportion of Ki67− stained tumor region within an ER-stained tumor region, a size variation of Ki67 positive tumor cells, an average eccentricity of Ki67 positive tumor blobs, an average density of Ki67 and neighbors within a 50 um radius around a Ki67+ cell, a heterogeneity of a Ki67+ staining intensity, a heterogeneity of a hematoxylin stain intensity within one or more Ki67+ tumor cells, or an interquartile range of a PR+ tumor cell size.

12. The system of claim 1, wherein the operations further comprise performing a registration operation between at least two of the plurality of images.

13. The system of claim 1, further comprising detecting tissue objects in an image of the plurality of images by counting a number of tumor nuclei or lymphocytes in the image.

14. A computer-implemented method comprising:
    accessing a plurality of images corresponding to a tissue sample, wherein a first image of the plurality of images is a hematoxylin-and-eosin (H&E) image and a second image of the plurality of images is an individually stained or a multiplex immunohistochemical (IHC) image;

detecting, for each image of the plurality of images, a plurality of marker-specific features, wherein each marker-specific feature of plurality of the marker-specific features corresponds to a tissue object represented in an image of the plurality of images;

computing a plurality of inter-marker features, wherein each of the inter-marker features is computed based on a first value derived from a marker-specific feature of the first image and a second value derived from a marker-specific feature of the second image;

training a breast-cancer recurrence model using the plurality of inter-marker features and a clinical outcome data of a subject associated with the tissue sample; and processing another image using the trained breast-cancer recurrence model to estimate a breast-cancer-risk recurrence score; and outputting the breast-cancer-risk recurrence score.

15. The computer-implemented method of claim 14, wherein the H&E image comprises an image of the tissue sample that is stained with one or more stains that highlight one or more structures in the tissue sample.

16. The computer-implemented method of claim 14, wherein the H&E image depicts morphological features within the tissue sample.

17. The computer-implemented method of claim 14, wherein said plurality of images corresponds to more than one tissue sample, each tissue sample of the more than one tissue sample being associated with a different subject and clinical outcome data corresponding to the different subject.

18. A non-transitory computer-readable storage medium storing instructions executable by a processor to perform operations comprising:

accessing a plurality of images corresponding to a tissue sample, wherein a first image of the plurality of images is a hematoxylin-and-eosin (H&E) image and a second image of the plurality of images is an individually stained or a multiplex immunohistochemical (IHC) image;

detecting, for each image of the plurality of images, a plurality of marker-specific features, wherein each marker-specific feature of plurality of the marker-specific features corresponds to a tissue object represented in an image of the plurality of images;

computing a plurality of inter-marker features, wherein each of the inter-marker features is computed based on a first value derived from a marker-specific feature of the first image and a second value derived from a marker-specific feature of the second image;

training a breast-cancer recurrence model using the plurality of inter-marker features and a clinical outcome data of a subject associated with the tissue sample; and processing another image using the trained breast-cancer recurrence model to estimate a breast-cancer-risk recurrence score; and outputting the breast-cancer-risk recurrence score.

19. The non-transitory computer-readable storage medium of claim 18, wherein the plurality of marker-specific features includes a nucleus blob shape feature, a nucleus blob area feature, a nucleus blob compactness feature, a nucleus blob density feature, a normalized color feature, an absolute color feature, a center vote strength, an annular region based feature, or a blob topography feature.

20. The non-transitory computer-readable storage medium of claim 18, wherein the plurality of marker-specific features and the plurality of inter-marker features includes a count of lymphocytes in a vicinity of a tumor region, a proportion of Ki67− stained tumor region within an ER-stained tumor region, a size variation of Ki67 positive tumor cells, an average eccentricity of Ki67 positive tumor blobs, an average density of Ki67 and neighbors within a 50 um radius around a Ki67+ cell, a heterogeneity of a Ki67+ staining intensity, a heterogeneity of a hematoxylin stain intensity within one or more Ki67+ tumor cells, or an interquartile range of a PR+ tumor cell size.

* * * * *

UNITED STATES PATENT AND TRADEMARK OFFICE
CERTIFICATE OF CORRECTION

| | | |
|---|---|---|
| PATENT NO. | : 11,288,795 B2 | Page 1 of 1 |
| APPLICATION NO. | : 16/659545 | |
| DATED | : March 29, 2022 | |
| INVENTOR(S) | : Michael Barnes, Srinivas Chukka and David Knowles | |

It is certified that error appears in the above-identified patent and that said Letters Patent is hereby corrected as shown below:

On the Title Page

(73) Assignee, add:
-- The Board of Trustees of the Leland Stanford Junior University, Palo Alto, CA (US) --

Signed and Sealed this
Twenty-fourth Day of September, 2024

Katherine Kelly Vidal
*Director of the United States Patent and Trademark Office*